(12) United States Patent
Alinsod et al.

(10) Patent No.: US 8,480,558 B2
(45) Date of Patent: Jul. 9, 2013

(54) IMPLANTS AND PROCEDURES FOR TREATMENT OF PELVIC FLOOR DISORDERS

(75) Inventors: Red Alinsod, San Juan Capistrano, CA (US); Stephen Wang, Grand Blanc, MI (US); Francois Blaudeau, Birmingham, AL (US); Sandra Muhlfeld, Thousand Oaks, CA (US); Bryon Merade, Thousand Oaks, CA (US); Ty Erickson, Idaho Falls, ID (US)

(73) Assignee: Caldera Medical, Inc., Agoura Hills, CA (US)

( * ) Notice: Subject to any disclaimer, the term of this patent is extended or adjusted under 35 U.S.C. 154(b) by 945 days.

(21) Appl. No.: 11/936,063

(22) Filed: Nov. 6, 2007

(65) Prior Publication Data
US 2008/0177132 A1    Jul. 24, 2008

Related U.S. Application Data

(60) Provisional application No. 60/864,521, filed on Nov. 6, 2006.

(51) Int. Cl.
*A61F 2/00* (2006.01)
(52) U.S. Cl.
USPC .......................................................... 600/37
(58) Field of Classification Search
USPC ................. 600/29–31, 37; 128/885; 606/151; 623/11.11
See application file for complete search history.

(56) References Cited

U.S. PATENT DOCUMENTS

| | | |
|---|---|---|
| 5,899,909 A | 5/1999 | Claren et al. |
| 5,902,015 A | 5/1999 | Allcock |
| 5,934,283 A | 8/1999 | Willem et al. |
| 6,010,447 A | 1/2000 | Kardjian |
| 6,042,534 A | 3/2000 | Gellman et al. |
| 6,050,937 A | 4/2000 | Benderev |
| 6,197,036 B1 | 3/2001 | Tripp et al. |
| 6,200,330 B1 | 3/2001 | Benderev et al. |
| 6,273,852 B1 | 8/2001 | Lehe et al. |
| 6,302,840 B1 | 10/2001 | Benderev |
| 6,328,686 B1 | 12/2001 | Kovac |
| 6,451,024 B1 | 9/2002 | Thompson et al. |
| 6,491,703 B1 | 12/2002 | Ulmsten |

(Continued)

FOREIGN PATENT DOCUMENTS

| | | |
|---|---|---|
| EP | 2081517 A2 | 7/2009 |
| GB | 2 353 220 A | 2/2001 |

(Continued)

OTHER PUBLICATIONS

WIPO, U.S. International Preliminary Examining Authority, International Preliminary Report on Patentability mailed Jul. 5, 2011 in International Patent Application No. PCT/US2010/020158, 1 page.

(Continued)

*Primary Examiner* — Christine Matthews
(74) *Attorney, Agent, or Firm* — Inskeep IP Group, Inc.

(57) ABSTRACT

Implants for the treatment of pelvic support conditions and methods of implementing the same. The implants comprise relatively soft, flexible bodies and relatively strong arms extending in predetermined orientation therefrom. Methods and devices for placing the implants minimize trauma to the pelvic floor and provide well-anchored support to pelvic organs without interfering with sexual or other bodily functions.

1 Claim, 17 Drawing Sheets

U.S. PATENT DOCUMENTS

| | | |
|---|---|---|
| 6,575,998 B2 | 6/2003 | Beyar |
| 6,592,515 B2 | 7/2003 | Thierfelder et al. |
| 6,595,911 B2 | 7/2003 | LoVuolo |
| 6,638,210 B2 | 10/2003 | Berger |
| 6,638,211 B2 | 10/2003 | Suslian et al. |
| 6,666,817 B2 | 12/2003 | Li |
| 6,685,626 B2 | 2/2004 | Wironen |
| 6,808,486 B1 | 10/2004 | O'Donnell |
| 6,808,487 B2 | 10/2004 | Migliari |
| 6,884,212 B2 | 4/2005 | Thierfelder et al. |
| 6,911,003 B2 | 6/2005 | Anderson et al. |
| 6,953,428 B2 | 10/2005 | Gellman et al. |
| 6,960,160 B2 | 11/2005 | Browning |
| 7,056,333 B2 | 6/2006 | Walshe |
| 7,131,943 B2 | 11/2006 | Kammerer |
| 7,131,944 B2 | 11/2006 | Jacquetin |
| 7,204,802 B2 | 4/2007 | De Leval |
| 7,229,404 B2 | 6/2007 | Bouffier |
| 7,303,525 B2 | 12/2007 | Watschke et al. |
| 7,351,197 B2 | 4/2008 | Montpetit et al. |
| 7,371,245 B2 | 5/2008 | Evans et al. |
| 7,393,319 B2 | 7/2008 | Merade et al. |
| 7,393,320 B2 | 7/2008 | Montpetit et al. |
| 7,494,495 B2 | 2/2009 | Delorme et al. |
| 7,500,945 B2 | 3/2009 | Cox et al. |
| 7,524,281 B2 | 4/2009 | Chu et al. |
| 7,527,588 B2 | 5/2009 | Zaddem et al. |
| 7,527,633 B2 | 5/2009 | Rioux |
| 7,559,885 B2 | 7/2009 | Merade et al. |
| 7,740,576 B2 * | 6/2010 | Hodroff et al. ............. 600/29 |
| 7,771,345 B1 * | 8/2010 | O'Donnell ............. 600/29 |
| 2002/0161382 A1 | 10/2002 | Neisz et al. |
| 2002/0188169 A1 | 12/2002 | Kammerer et al. |
| 2003/0023138 A1 | 1/2003 | Luscombe |
| 2003/0088270 A1 | 5/2003 | Lubbers et al. |
| 2003/0171644 A1 | 9/2003 | Anderson et al. |
| 2003/0176762 A1 | 9/2003 | Kammerer |
| 2003/0216814 A1 | 11/2003 | Siegel et al. |
| 2004/0039453 A1 | 2/2004 | Anderson et al. |
| 2004/0087970 A1 | 5/2004 | Chu et al. |
| 2004/0122474 A1 | 6/2004 | Gellman et al. |
| 2004/0143152 A1 | 7/2004 | Grocela |
| 2004/0144395 A1 | 7/2004 | Evans et al. |
| 2005/0004424 A1 | 1/2005 | Raz et al. |
| 2005/0004427 A1 | 1/2005 | Cervigni |
| 2005/0027160 A1 | 2/2005 | Siegel et al. |
| 2005/0075660 A1 | 4/2005 | Chu et al. |
| 2005/0177180 A1 | 8/2005 | Kaganov et al. |
| 2005/0261547 A1 | 11/2005 | Bouffier |
| 2006/0089524 A1 * | 4/2006 | Chu ............. 600/37 |
| 2006/0089525 A1 | 4/2006 | Mamo et al. |
| 2006/0130848 A1 | 6/2006 | Carey |
| 2006/0173237 A1 * | 8/2006 | Jacquetin ............. 600/29 |
| 2006/0229493 A1 | 10/2006 | Weiser et al. |
| 2006/0229596 A1 | 10/2006 | Weiser et al. |
| 2006/0247490 A1 | 11/2006 | Merade et al. |
| 2006/0260618 A1 | 11/2006 | Hodroff et al. |
| 2007/0021649 A1 | 1/2007 | Nowlin et al. |
| 2007/0043255 A1 | 2/2007 | O'Donnell |
| 2007/0055095 A1 | 3/2007 | Chu et al. |
| 2007/0156175 A1 | 7/2007 | Weadock et al. |
| 2007/0161849 A1 | 7/2007 | Goldberg |
| 2007/0161850 A1 | 7/2007 | Harari et al. |
| 2007/0173864 A1 | 7/2007 | Chu |
| 2007/0270890 A1 | 11/2007 | Miller |
| 2007/0299299 A1 | 12/2007 | Rosenblatt |
| 2008/0004487 A1 | 1/2008 | Haverfield |
| 2008/0004490 A1 | 1/2008 | Bosley, Jr. et al. |
| 2008/0021265 A1 | 1/2008 | Garbin et al. |
| 2008/0027271 A1 | 1/2008 | Maccarone |
| 2008/0033232 A1 | 2/2008 | Catanese, III et al. |
| 2008/0033488 A1 | 2/2008 | Catanese, III et al. |
| 2008/0039874 A1 | 2/2008 | Catanese, III et al. |
| 2008/0039894 A1 | 2/2008 | Catanese, III et al. |
| 2008/0081945 A1 | 4/2008 | Toso et al. |
| 2008/0082105 A1 | 4/2008 | Chu |
| 2008/0082121 A1 | 4/2008 | Chu |
| 2008/0097329 A1 | 4/2008 | Hodroff et al. |
| 2008/0132753 A1 | 6/2008 | Goddard |
| 2008/0140218 A1 | 6/2008 | Staskin et al. |
| 2008/0161837 A1 | 7/2008 | Toso et al. |
| 2008/0183031 A1 | 7/2008 | Montpetit et al. |
| 2008/0196729 A1 | 8/2008 | Browning |
| 2008/0208251 A1 | 8/2008 | Weadock et al. |
| 2008/0287956 A1 | 11/2008 | Smith et al. |
| 2008/0287968 A1 | 11/2008 | Smith et al. |
| 2009/0005633 A9 | 1/2009 | Montpetit et al. |
| 2009/0018387 A1 | 1/2009 | Veronikis |
| 2009/0023982 A1 | 1/2009 | Karram |
| 2009/0105526 A1 | 4/2009 | Piroli Torelli et al. |
| 2009/0156891 A1 | 6/2009 | Heys et al. |
| 2009/0171139 A1 | 7/2009 | Chu |
| 2009/0171140 A1 | 7/2009 | Chu |
| 2009/0171142 A1 | 7/2009 | Chu et al. |
| 2009/0171143 A1 | 7/2009 | Chu et al. |
| 2009/0171377 A1 | 7/2009 | Intoccia et al. |
| 2009/0192346 A1 | 7/2009 | Rosenblatt |
| 2009/0192347 A1 | 7/2009 | Davila et al. |
| 2009/0216075 A1 | 8/2009 | Bell et al. |
| 2009/0222025 A1 | 9/2009 | Catanese, III et al. |

FOREIGN PATENT DOCUMENTS

| | | |
|---|---|---|
| WO | WO 97/07744 | 3/1997 |
| WO | WO 02/38079 A3 | 5/2002 |
| WO | WO 02/078571 A2 | 10/2002 |
| WO | WO 03/073960 A1 | 9/2003 |
| WO | WO 03/105727 A1 | 12/2003 |
| WO | WO 2004/012579 A3 | 2/2004 |
| WO | WO 2004/012626 A1 | 2/2004 |
| WO | WO 2005/072626 A1 | 8/2005 |
| WO | WO 2007/084411 A2 | 7/2007 |
| WO | WO 2008/058163 A2 | 5/2008 |
| WO | WO 2010/078591 A1 | 7/2010 |
| WO | WO 2010/078593 A1 | 7/2010 |
| WO | WO 2010/078595 A1 | 7/2010 |

OTHER PUBLICATIONS

WIPO, U.S. International Preliminary Examining Authority, International Preliminary Report on Patentability mailed Jul. 5, 2011 in International Patent Application No. PCT/US2010/020151, 1 page.

United States Patent and Trademark Office, Office Action mailed May 26, 2011 in U.S. Appl. No. 12/145,417, 9 pages.

Canadian Intellectual Property Office, Office Action dated Apr. 27, 2011 in Canadian Patent Application No. 2,542,873, 3 pages.

WIPO, U.S. International Search Authority, International Search Report and Written Opinion mailed Mar. 8, 2010 in International Patent Application No. PCT/US10/20151, 8 pages.

WIPO, U.S. International Search Authority, International Search Report and Written Opinion mailed Feb. 26, 2010 in International Patent Application No. PCT/US2010/020158, 7 pages.

WIPO, U.S. International Search Authority, International Search Report and Written Opinion mailed Feb. 26, 2010 in International Patent Application No. PCT/US2010/020161, 7 pages.

European Patent Office, First Examination Report dated Oct. 27, 2009 in European Patent Application No. 04 794 132.3-2320, 4pp.

European Patent Office, Examination Report dated Jun. 16, 2009 in European Patent Application No. 07844920.4-1257, 2pp.

WIPO, U.S. International Preliminary Examining Authority, International Preliminary Report on Patentability mailed May 12, 2009 in International Patent Application No. PCT/US2007/083844, 1 page.

United States Patent and Trademark Office, Office Action mailed Mar. 18, 2009 in U.S. Appl. No. 10/947,182, 8 pages.

European Patent Office, Supplementary European Search Report dated Apr. 28, 2008 in European Patent Application No. 04794132.3-2310, 4pp.

WIPO, U.S. International Search Authority, International Search Report and Written Opinion mailed Apr. 15, 2008 in International Patent Application No. PCT/US07/83844, 9 pages.

United States Patent and Trademark Office, Office Action mailed Apr. 4, 2008 in U.S. Appl. No. 10/947,182, 8 pages.

United States Patent and Trademark Office, Notice of Allowance mailed Apr. 2, 2008 in U.S. Appl. No. 10/684,861, 5 pages.

United States Patent and Trademark Office, Final Office Action mailed Dec. 12, 2007 in U.S. Appl. No. 10/947,182, 7 pages.

United States Patent and Trademark Office, Office Action mailed Aug. 21, 2007 in U.S. Appl. No. 11/119,446, 12 pages.

WIPO, U.S. International Search Authority, International Search Report and Written Opinion mailed Jul. 23, 2007 in International Patent Application No. PCT/US2007/000920, 10 pages.

United States Patent and Trademark Office, Office Action mailed May 10, 2007 in U.S. Appl. No. 10/947,182, 9 pages.

WIPO, U.S. International Search Authority, International Search Report and Written Opinion mailed Apr. 4, 2007 in International Patent Application No. PCT/US06/16709, 12 pages.

United States Patent and Trademark Office, Office Action mailed Mar. 15, 2007 in U.S. Appl. No. 10/684,861, 8 pages.

Almeida, Silvio H.M., et al., Use of Cadaveric Fascia Lata to Correct Grade IV Cystocele, *International Braz J Urol* vol. 29(1):48-51, Jan.-Feb. 2003, 5 pages.

Chon, J. et al., "Results of the Transvaginal Cadaveric Prolapse Repair with Sling (CaPS)," presented at International Continence Society 32nd Annual meeting, Heidelberg, Germany, 2002, p. 150, 1 page.

Kobashi, K.C. et al., "The Use of Solvent-Dehydrated Cadaveric Fascia Lata (Tutoplast) in Slings and Cystocele Repairs: The Virginia Mason Experience," presented at International Continence Society 32nd Annual meeting, Heidelberg, Germany, 2002, p. 151, 1 page.

Kobashi, K.C. et al., "A New Technique for Cystocele Repair and Transvaginal Sling: The Cadaveric Prolapse Repair and Sling (CaPS)," *Urology* 56:9-14 (Supplement 6A), Dec. 2000, 6 pages.

\* cited by examiner

IMPLANTS AND PROCEDURES FOR TREATMENT OF PELVIC FLOOR DISORDERS

RELATED APPLICATIONS

This application claims priority to U.S. Provisional Application Ser. No. 60/864,521 filed Nov. 6, 2006 entitled Implant And Procedure For Treatment Of Pelvic Floor Disorders which is hereby incorporated by reference.

BACKGROUND OF THE INVENTION

Pelvic floor disorders are a class of abnormalities that affect the pelvic region of patients, and they afflict millions of men and women. In women, for example, the pelvic region includes various anatomical structures such as the uterus, the rectum, the bladder, and the vagina. These anatomical structures are supported and held in place by a complex collection of tissues, such as muscles and ligaments. When these tissues are damaged, stretched, or otherwise weakened, the anatomical structures of the pelvic region shift and in some cases protrude into other anatomical structures. For example, when the tissues between the bladder and the vagina weaken, the bladder may shift and protrude into the vagina, causing a pelvic floor disorder known as cystocele. Other pelvic floor disorders include vaginal prolapse, vaginal hernia, rectocele, enterocele, uterocele, and/or urethrocele.

Pelvic floor disorders often cause or exacerbate urinary incontinence (UI). One type of UI, called stress urinary incontinence (SUI), effects primarily women and is often caused by two conditions—intrinsic sphincter deficiency (ISD) and hypermobility. These conditions may occur independently or in combination. In ISD, the urinary sphincter valve, located within the urethra, fails to close (or "coapt") properly, causing urine to leak out of the urethra during stressful activity. In hypermobility, the pelvic floor is distended, weakened, or damaged. When the afflicted woman sneezes, coughs, or otherwise strains the pelvic region, the bladder-neck and proximal urethra rotate and descend. As a result, the urethra does not close with sufficient response time, and urine leaks through the urethra.

UI and pelvic floor disorders, which are usually accompanied by significant pain and discomfort, are often treated by implanting a supportive sling or mesh in or near the pelvic floor region to support the fallen or shifted anatomical structures or more generally, to strengthen the pelvic region by promoting tissue in-growth. Often, treatments of stress incontinence are made without treating the pelvic floor disorders at all, potentially leading to an early recurrence of the stress incontinence.

Existing systems, methods, and kits for treatment typically apply delivery devices to position a supportive surgical implant into a desired position in the pelvic region. However, some of these systems and methods require a medical operator to create multiple incisions and deliver the implant using complex procedures. Moreover, many existing surgical implants are not suitably sized or shaped to properly fit within a patient and treat pelvic floor disorders. Accordingly, medical operators and patients need improved systems, methods, and surgical kits for the treatment of pelvic floor disorders and/or urinary incontinence.

SUMMARY OF THE INVENTION

The present invention provides improved methods and devices for supporting pelvic organs in the treatment of conditions such as incontinence and various pelvic floor disorders including but not limited to cystocele, enterocele and rectocele.

Devices of the present invention include implants having soft, flexible support bodies and anchor arms that are sturdy and durable.

Other devices of the present invention include introducers that allow an implant to be deeply implanted so as not to cause damage to the pelvic floor and to preserve the natural length of the vagina.

Methods of the present invention include the use of multiple implants for treating multiple disorders, including treating pelvic floor disorders and incontinence.

DETAILED DESCRIPTION OF THE PREFERRED EMBODIMENT

Devices
Anterior Compartment Implant

Figure 1:
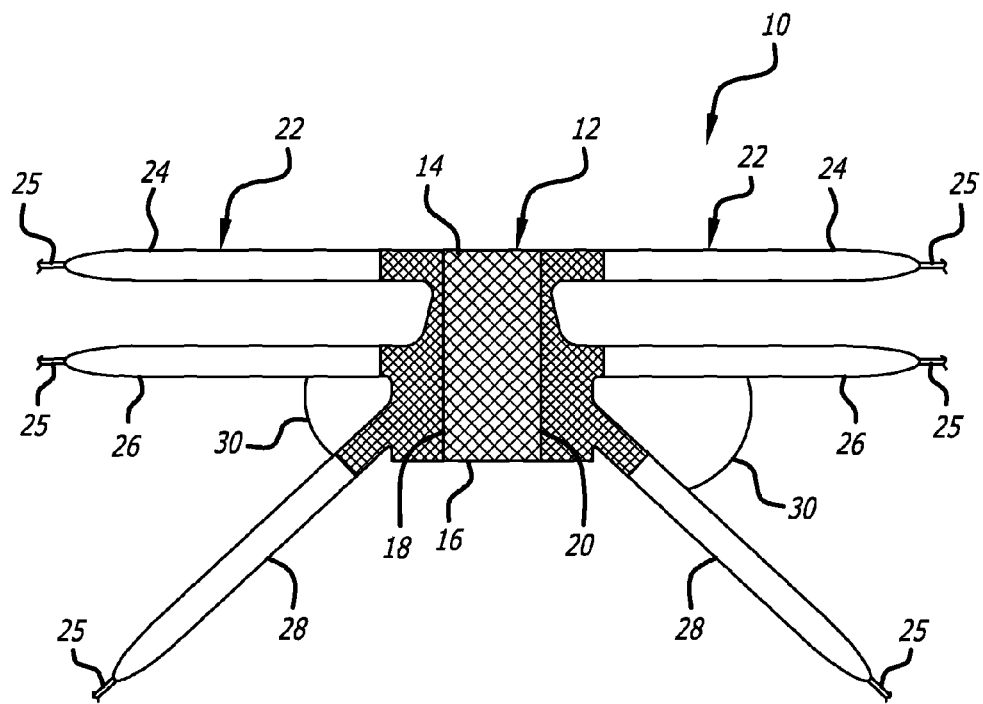
FIG. 1 is a plan view of an embodiment of an anterior implant of the present invention.

Referring to FIG. 1 there is shown an embodiment of an anterior compartment implant 10 of the present invention that provides both anchoring and support to the bulbar urethral complex of a male patient or the bladder and the vagina including the apex of the vagina of a female patient. The implant 10 generally includes a body 12 that has a first end 14 and a second end 16 opposite the first end 14. Preferably, the body 12 is a flat panel formed of a mesh material that extends to side extents 18 and 20.

The implant 10 also includes arm portions 22 that extend outwardly from the body 12 on either side of the side extents 18 and 20. The side extents 18 and 20 can extend out laterally to the arms 24, 26, and 28. The arm portions of the implant 10 of FIG. 1 collectively include a plurality of arms that can be divided by function into three pairs: first pair 24, second pair 26 and third pair 28. Preferably, the arm portions 22 are cut from flat panels formed of a mesh material. The arm portions 22 may be formed separately from the body 12 and then attached thereto using sutures, adhesive, heat treatment or a variety of other techniques. Preferably, however, the arm portions 22 are formed in conjunction with the body 12 (hereinafter "unibody construction") such that subsequent attachment is not necessary and risks associated with attached arm portions (separation, frayed edges, ridges, etc.) are eliminated. More preferably, the meshwork of the implant 10 has more than one zone, each zone having the ability to be constructed of a different filament diameter, stitch pattern, mesh density, or any combination of the three, such that the body 12 is macroporous, supple, and flexible, while the mesh of the arm portions 22 is more supportive while also macroporous. In a most preferred embodiment, the multiple zone concept is incorporated into the unibody construction concept.

For example, one preferred embodiment includes a mesh body panel 12 that is formed by knitting filaments having a diameter of approximately 3 mils into a relatively open, porous pattern. The arm portions 22 are formed by knitting filaments having a diameter of approximately 6.5 mils in a pattern that is tighter than the pattern used in knitting the body 12. Other size filaments are also within the scope of the invention, the nature of the invention being that the body panel 12 has smaller diameter filaments as compared to arm portions 22. The arm portions 22 are knitted together with the body 12 such that the implant 10 has a unibody construction.

Because the body 12 is constructed of mesh, the shape of the body 12 is easily modifiable by simply cutting the body 12 to a desired shape. Hence, if a patient is smaller than average, the body 12 may be reduced, for instance, by trimming the first end 14 and/or the second end 16. In order to provide confidence that an appropriate size is attained prior to surgery, templates may be provided based on certain patient size criteria, that allows the body 12 to be trimmed to a corresponding size. For example, a template for a patient having a certain height or weight may be used to approximate a size and shape for a desired implant body 12 that should correspond to the patient anatomy. Other patient criteria, such as pelvic bone width, may be used as an entering argument for template selection.

The three pairs of arms 24, 26 and 28 of the implant 10 make the implant 10 ideally suited as an anterior compartment implant and provide apical support. Each arm preferably includes a suture (e.g., string, cord, line, wire, rope, metal, etc.) loop 25 at its end for attachment to an introducer. The first pair of arms are generally flush with the first end 14 of the body 12 and extend directly out therefrom. The second arms 26 are adjacent, and generally parallel to the first arms 24. In place, the first and second pairs of arms 24 and 26 are routed through the obturator fossa and up into the dermis where they are anchored. The third arms 28 are adjacent to and extend at an angle 30 to the second arms 26. The third pair of arms 28 are designed for passage through the ischiorectal fossa for apical suspension and the angle 30 is chosen for anatomical placement without folds. Alternatively, the arms 28 can be trimmed for attachment to the sacrospinous ligament for apical suspension. The angle 30 is preferably a non-zero angle, is more preferably between 30 and 60 degrees and is shown as being approximately 45 degrees.

The arms 24, 26 and 28 are all relatively slender and long. The width of the arms is sufficient to provide structural support, yet thin enough to pass through tissue without undue effort. The widths of arms 24, 26 and 28 are preferably between 0.1 and 2 cm, more preferably between 0.5 and 1.5 cm and even more preferably approximately 1 cm. In the embodiment of implant 10 shown in FIG. 1, the arms 24, 26 and 28 have a preferred width of 1.1 cm. The length of the arms 24, 26 and 28 are long enough to pass through the incisions and out of the body. As they are trimmed in a final step of the implantation, the length needs simply be long enough to allow ease of installation. In the embodiment of FIG. 1, the arms 24, 26 and 28 are each longer than 15 cm, closer to 19 cm, and have 5 cm long tapered ends to aid in installation.

Figure 2:
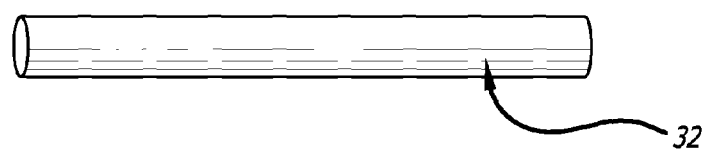
FIG. 2 is a perspective view of an embodiment of a sleeve of the present invention.

Sleeves 32, such as the one shown in FIG. 2, that are sized to fit over the arms 24, 26 and 28 and constructed of a smooth, slippery material, may be applied over the arms 24, 26 and 28 to further assist in passing the arms through tissue incisions and help reduce the spread of any infection from one part of a patient to another. These sleeves are then removed after the arms have been passed through the tissue such that tissue ingrowth may occur.

Posterior Compartment Implant

Figure 3:
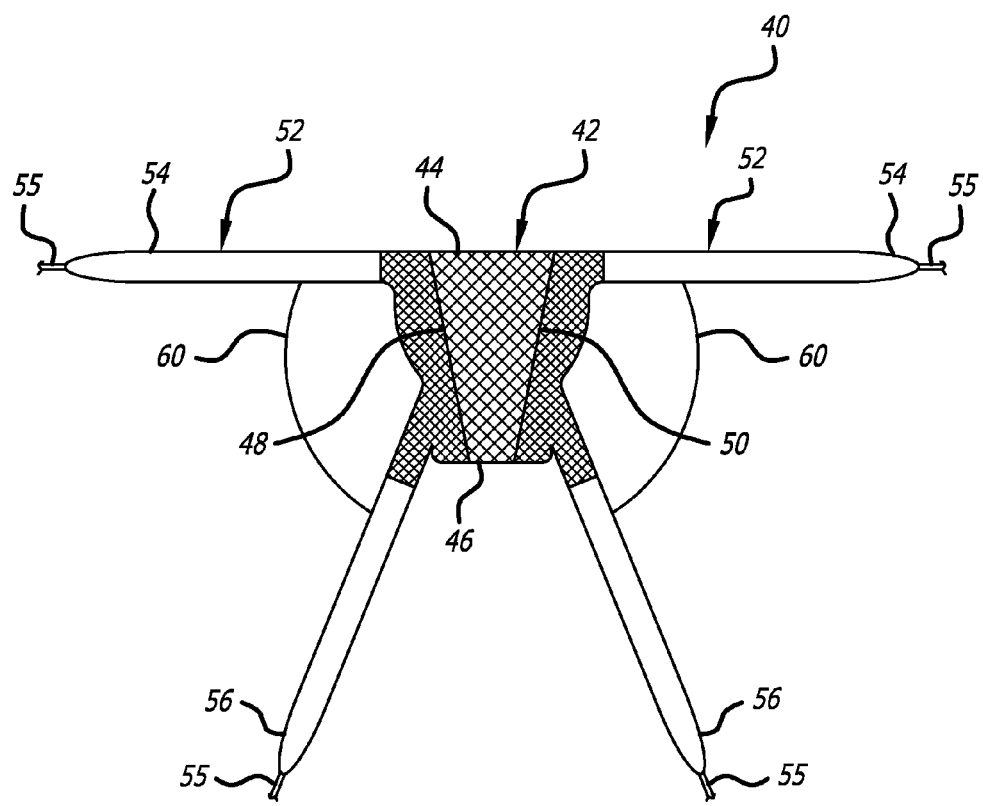
FIG. 3 is a plan view of an embodiment of a posterior implant of the present invention.

Referring to FIG. 3 there is shown an embodiment of a posterior compartment implant 40 of the present invention that provides both anchoring and support to the pelvic structures of a male patient or the rectum, perineum, vagina and the apex of the vagina of a female patient. The implant 40 generally includes a body 42 that has a first end 44 and a second end 46 opposite the first end 44. Preferably, the body 42 is a flat panel formed of a mesh material that extends to side extents 48 and 50.

The implant 40 also includes arm portions 52 that extend outwardly from the body 42 on either side of the side extents 48 and 50. The side extents 48 and 50 can extend out laterally to the arms 54 and 56. The arm portions 52 of the implant 40 of FIG. 3 collectively include a plurality of arms that can be divided by function into two pairs: first pair 54 and a second pair 56. Preferably, the arm portions 52 are cut from flat panels formed of a mesh material. The arm portions 52 may be formed separately from the body 42 and then attached thereto using sutures, adhesive, heat treatment or a variety of other techniques. Preferably, however, the arm portions 52 and the body 42 are of unibody construction such that subsequent attachment is not necessary and risks associated with attached arm portions (separation, frayed edges, ridges, etc.) are eliminated. More preferably, the meshwork of the implant 40 has more than one zone, each zone having the ability of being constructed of a different filament diameter, stitch pattern, mesh density, or a combination of all three, such that the body 42 is macroporous, supple, and flexible, while the mesh of the arm portions 52 is more supportive while also macroporous. In a most preferred embodiment, the multiple zone concept is incorporated into the unibody construction concept.

For example, one preferred embodiment includes a mesh body panel 42 that is formed by knitting filaments having a diameter of approximately 3 mils into a relatively open, porous pattern. The arm portions 52 are formed by knitting filaments having a diameter of approximately 6.5 mils in a pattern that is tighter than the pattern used in knitting the body 42. Other size filaments are also within the scope of the invention, the nature of the invention being that the body panel 42 has smaller diameter filaments as compared to arm portions 52. The arm portions 52 are knitted together with the body 42 such that the implant 40 has a unibody construction.

Because the body 42 is constructed of a flat mesh, the shape of the body 42 is easily modifiable by simply cutting the body 42 to a desired shape. Hence, if a patient is smaller than average, the body 42 may be reduced, for instance, by trimming the first end 44 and/or the second end 46. In order to provide confidence that an appropriate size is attained prior to surgery, templates may be provided based on certain patient size criteria, that allows the body 42 to be trimmed to a corresponding size. For example, a template for a patient having a certain height or weight may be used to approximate a size and shape for a desired implant body 42 that should correspond to the patient anatomy. Other patient criteria, such as pelvic bone width, may be used as an entering argument for template selection.

The two pairs of arms 54 and 56 of the implant 40 make the implant 40 ideally suited as an posterior compartment implant. Each arm preferably includes a sutured (e.g., string, cord, line, wire, rope, metal, etc.) loop 55 at its end for attachment to an introducer. The first pair of arms are generally flush with the first end 44 of the body 42 and extend directly out therefrom. In place, the first arms 54 are routed through the ischiorectal fossa and up into the dermis and exit via pararectal incisions where they are anchored, with the first end 44 sutured to the apex of the vagina to provide apical support. The second arms 56 extend at an angle 60 to the first arms 54. The second arms 56 are designed to anchor the implant to the perineum and pass through pararectal incisions and the angle 60 is chosen for anatomical placement without folds. The angle 60 is preferably a non-zero angle, is more preferably between 30 and 90 degrees and is shown as being approximately 75 degrees.

The arms 54 and 56 are all relatively slender and long. The width of the arms is sufficient to provide structural support, yet thin enough to pass through tissue without undue effort. The widths of arms 54 and 56 are preferably between 0.1 and 2 cm, more preferably between 0.5 and 1.5 cm and even more preferably approximately 1 cm. In the embodiment of implant 10 shown in FIG. 3, the arms 54 and 56 have a preferred width of 1.1 cm. The length of the arms 54 and 56 are long enough to pass through the incisions and out of the body. As they are trimmed in a final step of the implantation, the length needs simply be long enough to allow ease of installation. In the embodiment of FIG. 3, the arms 54 and 56 are each longer than 10 cm, with the first arms 54 closer to 19 cm and the second arms 56 closer to 15 cm. The arms 54 and 56 may have tapered ends to aid in installation.

Sleeves 32, such as the one shown in FIG. 2, that are sized to fit over the arms 54 and 56 and constructed of a smooth, slippery material, may be applied over the arms 54 and 56 to further assist in passing the arms through tissue incisions and help reduce the spread of any infection from one part of a patient to another. These sleeves are then removed after the arms have been passed through the tissue such that tissue ingrowth may occur.

Examples of other devices and methods used to treat disorders are described in U.S. application Ser. No. 11/674,962 entitled Implantable Sling For The Treatment Of Incontinence And Method Of Using The Same, filed Feb. 14, 2007; U.S. application Ser. No. 11/119,446 entitled Implantable Sling For The Treatment Of Incontinence And Method Of Using The Same, filed Apr. 30, 2005 and U.S. application Ser. No. 11/552,484 entitled Implantable Sling For The Treatment Of Male Incontinence And Method Of Using The Same filed on Oct. 24, 2006, all of which are herein incorporated by reference in their entireties.

Materials suitable for use in constructing the implants 10 and 40 of the present invention may include either synthetic materials, such as surgical mesh and the like, natural tissues, such as tissues harvested from either animal, cadaverous source or the patient themselves, and/or combinations of synthetic and natural materials. One embodiment of the present invention incorporates a colored mesh, such as a blue mesh, to improve the ease of locating the mesh during placement or removal and any subsequent surgical procedures. Additionally, the arms or the tips of the implants 10 and 40 may be color coded to allow the surgeon to identify each arm and the appropriate placement without confusion in a reproducible fashion.

Figure 4:
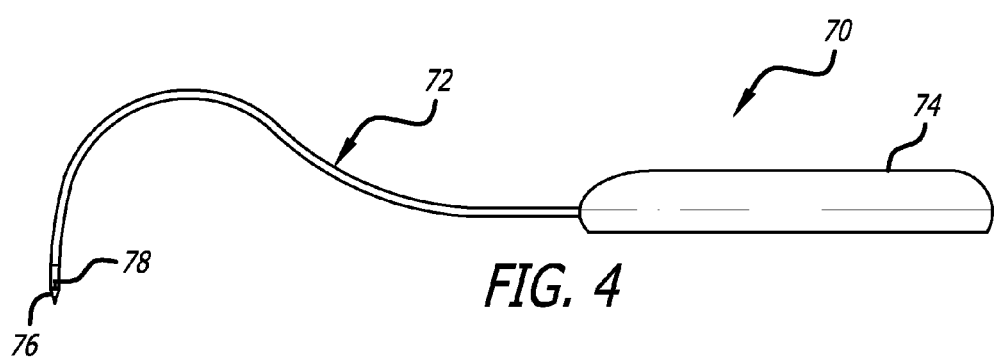
FIG. 4 is a plan view of an embodiment of an introducer of the present invention.
Figure 5:
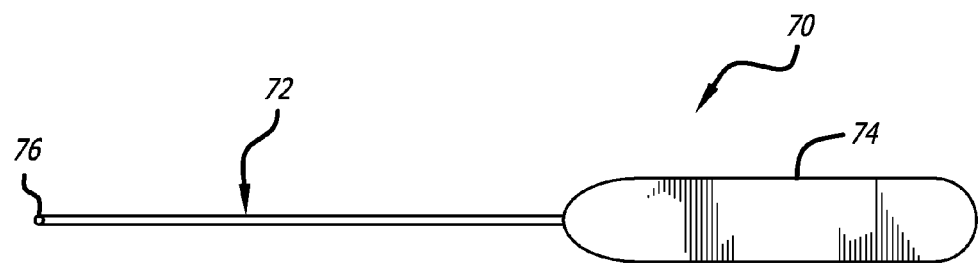
FIG. 5 is a side view of the introducer of FIG. 4.

Referring to FIGS. 4 and 5, there is shown an introducer 70, more specifically an inferior transobturator introducer 70, of the present invention. The introducer 70 generally includes a shaft 72 and a handle 74. The shaft 72 has a substantially straight portion, a transition portion and a curved portion. The shaft 72 is shaped to allow a deep pass that reaches the ischial spine or other anatomical structure to provide good apical support and to preserve the depth of the vagina after the implant is in place. In a preferred embodiment, the deep pass reaches the ischial spine which in a average size patient would be a distance of 7-10 cm. The shaft 72 has a distal end 76 that includes a slot 78 shaped to receive a suture loop 25 of the implant 10. The introducer 70 has a new and innovative shape. However, it is to be understood that prior introducers may also be used with the method and devices of the present invention. Many of these prior art introducers are described in the aforementioned incorporated references.

Figure 5A:
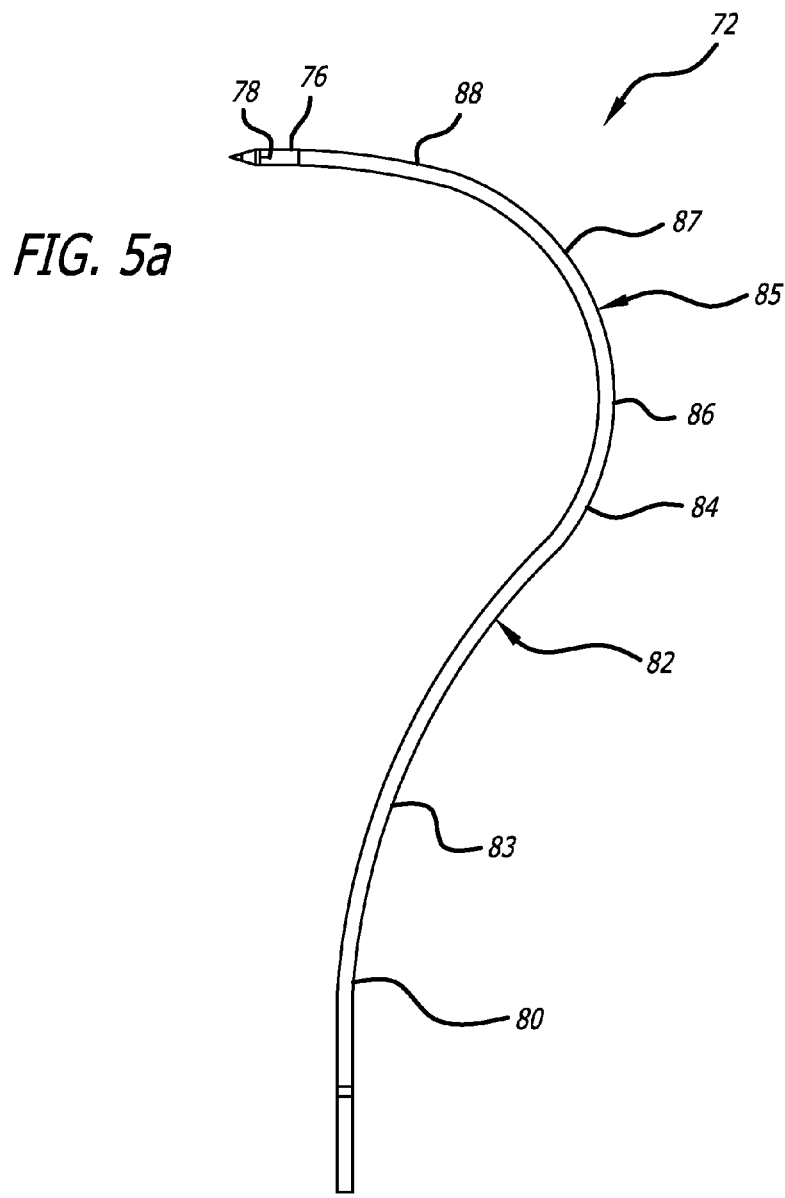
FIG. 5a is an elevation of a preferred embodiment of an introducer of the present invention.

FIG. 5a shows just one specific embodiment of a shaft 72 of introducer 70. The shaft 72 has a diameter of 3.5 mm and has a substantially straight portion 80 that is 2.28 cm long, 1.54 of which extends from the handle 74. The shaft 72 has a transition portion 82 that includes two curves 83 and 84. The first curve 83 has a radius of 7.14 cm and extends in a distal direction 2.04 cm. The second curve 84 has a radius of 5.34 cm and extends in a distal direction 1.42 cm. The curved portion 85 includes three curves; a first curve 86 having a radius of 2.05 cm and extends distally 1.93 cm, a second curve 87 having a radius of 1.39 cm and extending distally 0.83 cm, and a third curve 88 having a radius of 4.66 cm and extending distally 0.31 cm. The distal end 76 is the distal most part of the third curve 88.

Figure 6:
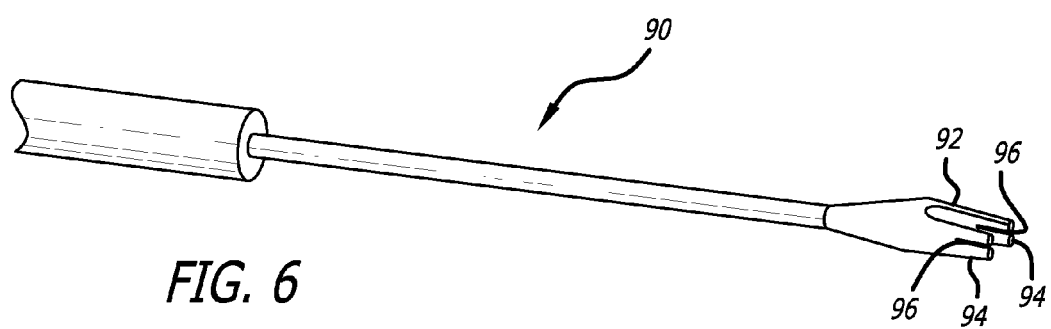
FIG. 6 is a perspective view of an attachment device of the present invention.

FIG. 6 shows an attachment device 90 of the present invention. The attachment device 90 includes a distal forked tip 92 that has two tines 94, each of which has a slot 96. A suture loop 25 or 55 may be placed through the slots 96 and the attachment device 90 can then be used to extend the reach of the physician to assist in attaching an arm of an implant to an introducer, as will be described in more detail below. Not only is the physician's reach extended, but using the slender attachment device 90 rather than reaching manually with the hand or forcing an introducer towards the introitus, reduces the risk of tearing fascia that supports the pelvic structures.

Implant Methods

The implants of the present invention may be used separately or together, based on the needs of the patient. They may also be used in connection with a sling implant for the treatment of treat urinary incontinence.

Anterior Compartment Implant

Figure 7:
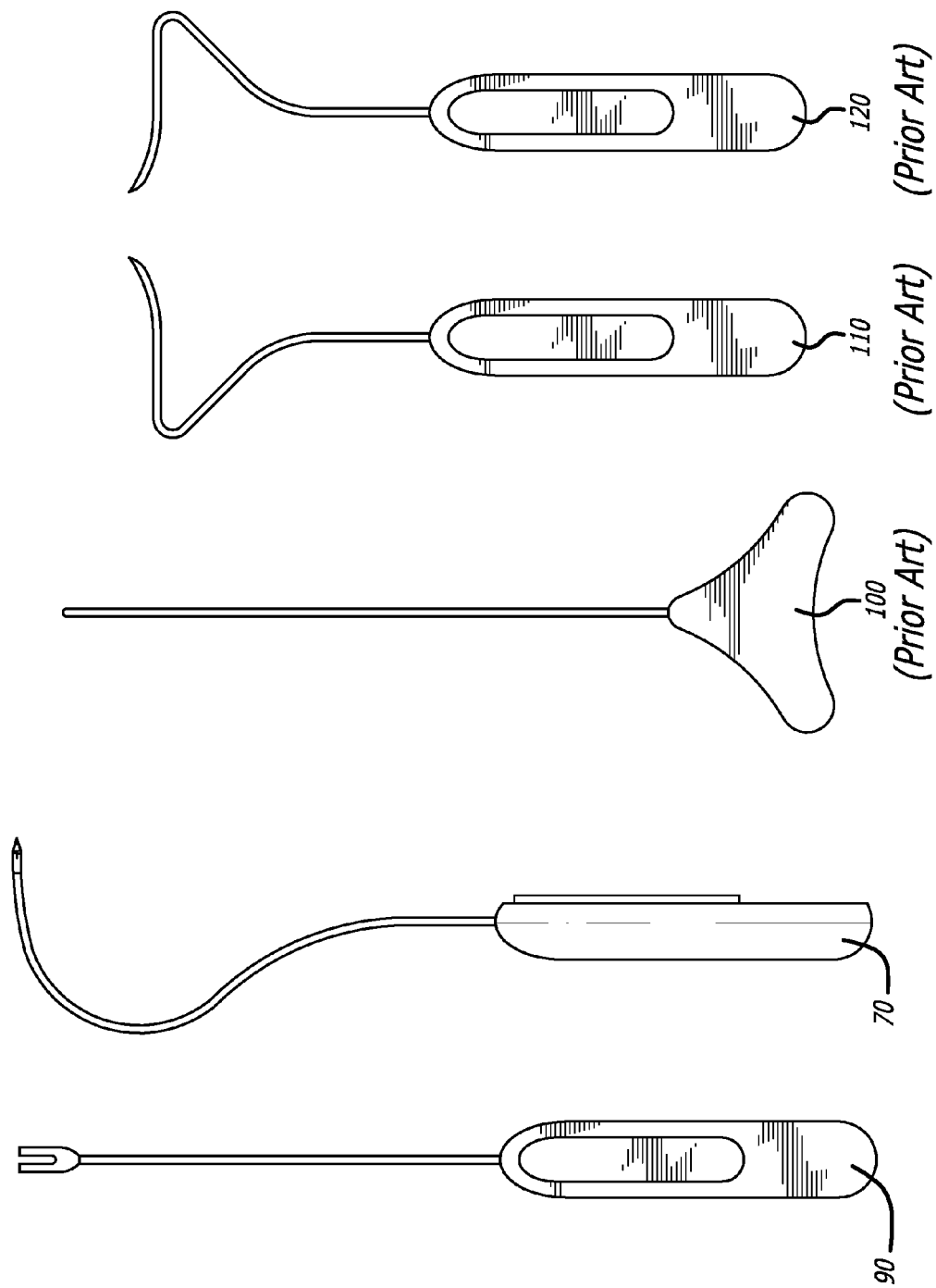
FIG. 7 is a top view of introducers used in accordance with the present invention.

Referring to FIGS. 7-21 one method of placing an anterior compartment implant 10 as contemplated for use in the present invention is illustrated that includes a surgical procedure as follows. In FIG. 7, the preferred instruments are gathered and sterilized, if necessary. They include (from left to right), the suture attachment device 90, the inferior transobturator introducer 70, a posterior introducer 100 (prior art), a right helical obturator introducer 110 (prior art) and a left helical obturator introducer 120 (prior art). One skilled in the art will realize that other introducers, such as hook introducers, suprapubic introducers, or transvaginal introducers may be substituted, especially for the helical obturator introducers 110 and 120.

The patient is given local, general, spinal, or epidural anesthetic. Pre and intra-op and post-op antibiotics are recommended. If the patient is female, she is placed in dorsal lithotomy stirrups and standard sterile preparations are performed. Vaginal retraction for access and view are recommended. A weighted speculum and lateral retraction will make the procedure easier to perform. Sterile saline, diluted local anesthetic with epinephrine, diluted vasopressin, or other solution should be injected underneath the vaginal mucosa for aqua dissection and to help with hemostasis. The injection can be done from at or below the mid urethra all the way to the lateral sidewalls and vaginal apex.

A midline incision in the anterior vaginal wall should be made starting 1 cm below the urethral meatus and extend it to approximately 2-3 cm short of the cuff or cervix. The vaginal mucosa should be dissected away from the bladder laterally to the vaginal sidewalls, and levator ani, and obturator internus, to the ischial spines on both sides and all the way to the apex or cervix. In one embodiment of the procedure of the present invention, three or more interrupted sutures are placed next to the apex of the vagina. These sutures will later be attached to the implant 10 second end 16 for apical support.

The obturator fossa is located and identified. It lays beneath the adductor longus and is generally at the level of the clitoris, and is underneath the crural folds. The thumb is used externally and index finger used internally to identify the obturator fossa. A 1 cm incision is made along the superior medial edge of the obturator fossa at the level of the inferior portion of the clitoris for a first arm 24 of the implant 10. A second 1 cm incision is made at the inferior border of the obturator fossa 2 cm lateral and 3 cm below the first incision for a second arm 26 of the implant 10. The incisions may be expanded with a small clamp if needed. These steps are repeated on the opposite obturator fossa.

Figure 8:
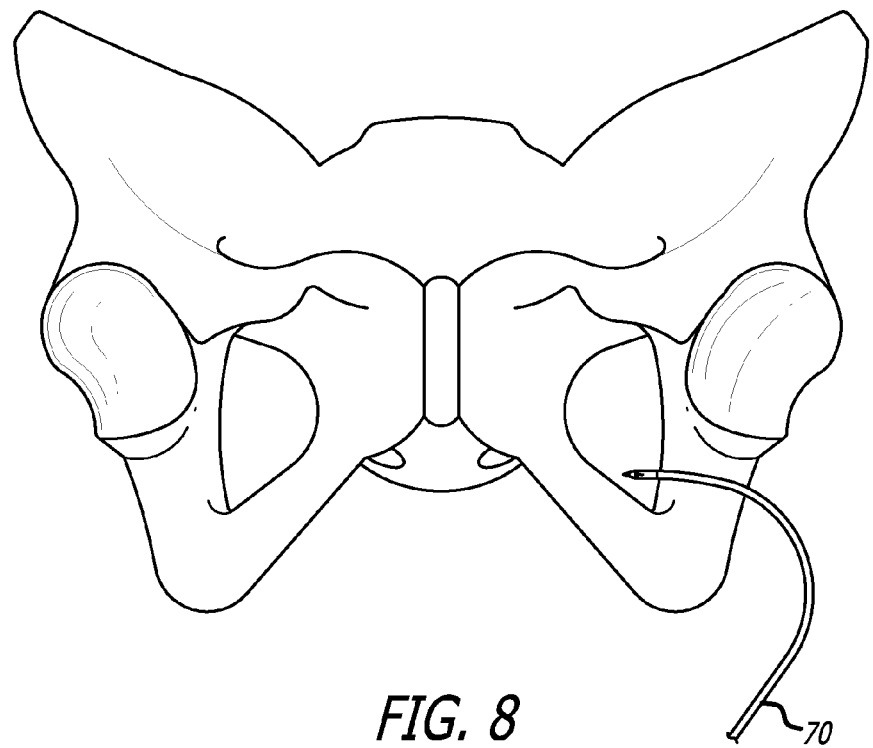
FIGS. 8-21 are a series of illustrations depicting various steps in a method of placing an anterior implant of the present invention; and, FIGS. 22-26 are a series of illustrations depicting various steps in a method of placing a posterior implant of the present invention.
Figure 9:
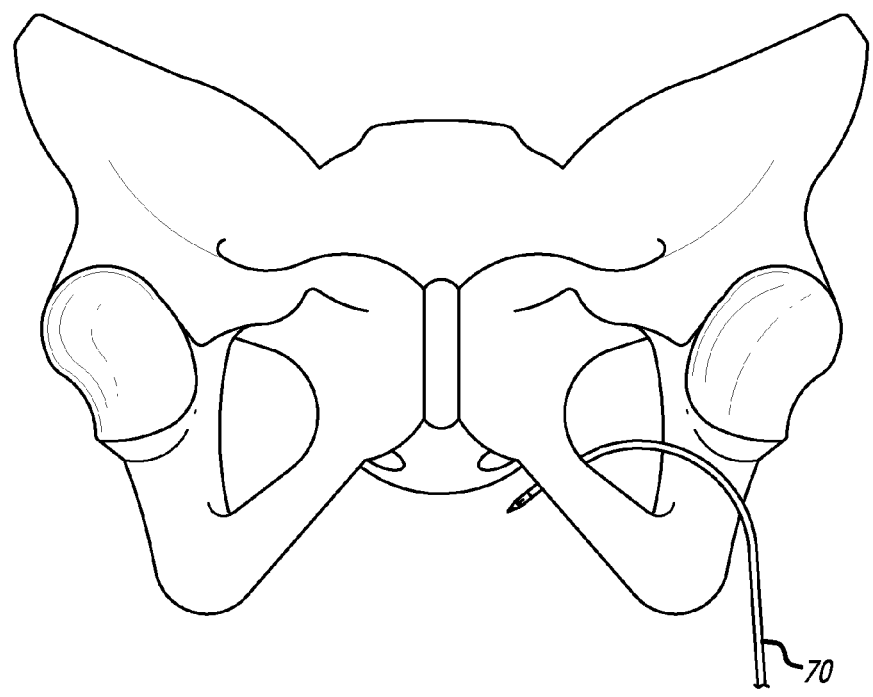

Referring to FIG. 8, the tip 76 of the inferior transobturator introducer 70 is inserted into the inferior medial groin incision (lower incision) to puncture through the obturator membrane and direct the introducer tip towards the ischial spine or vaginal apex. The tip 76 of the introducer 70 is identified through palpation and punched through the obturator internus muscle with gentle rotation and pressure. The vaginal index and/or middle fingers are used to guide the introducer tip through the fascial wall to exit proximally at the vaginal apex above the ischial spine. The introducer 70 is rotated to externalize the introducer tip 76 at the introitus. However, in a preferred embodiment the introducer 76 is not guided to the introitus rather it is left deep within the pelvis to preserve the pelvic support structures, as shown in FIG. 9.

Figure 10:
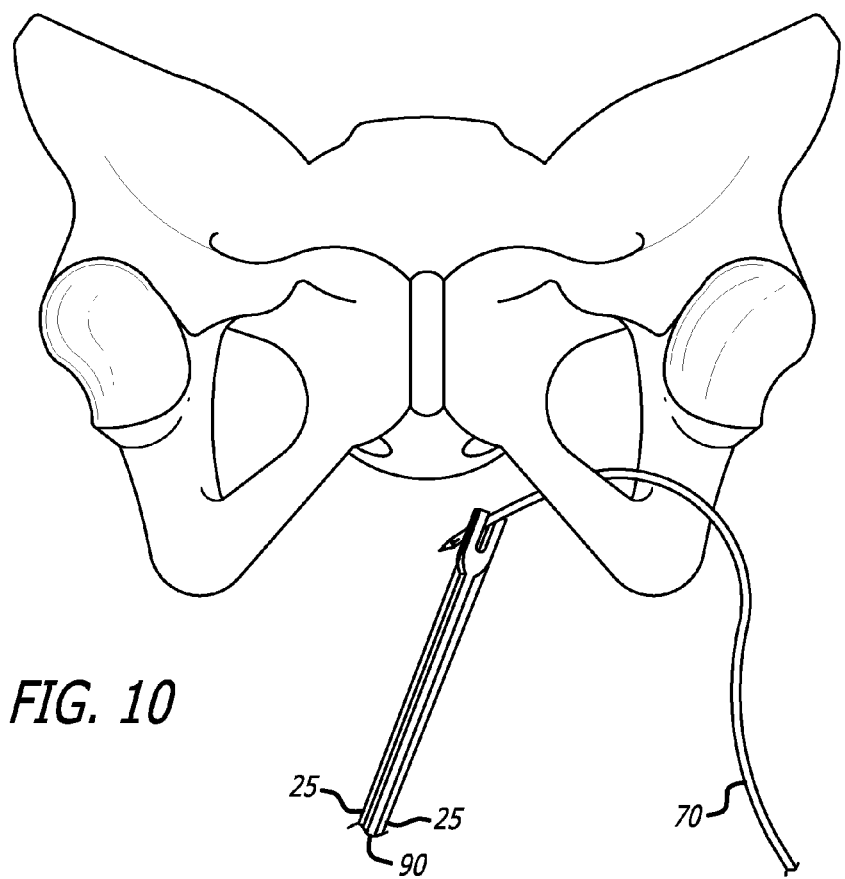

As illustrated in FIG. 10, next a second arm 26 of the implant 10 is identified and the loop 25 is placed through the notch 78 of the inferior introducer 70. Preferably, the sutures 25 are loaded onto the introducer 70 using the attachment device 90. Using the attachment device 90 obviates the need to pull the tip of the introducer 70 back toward the finger tips, potentially tearing the pelvic floor support structures.

Figure 11:
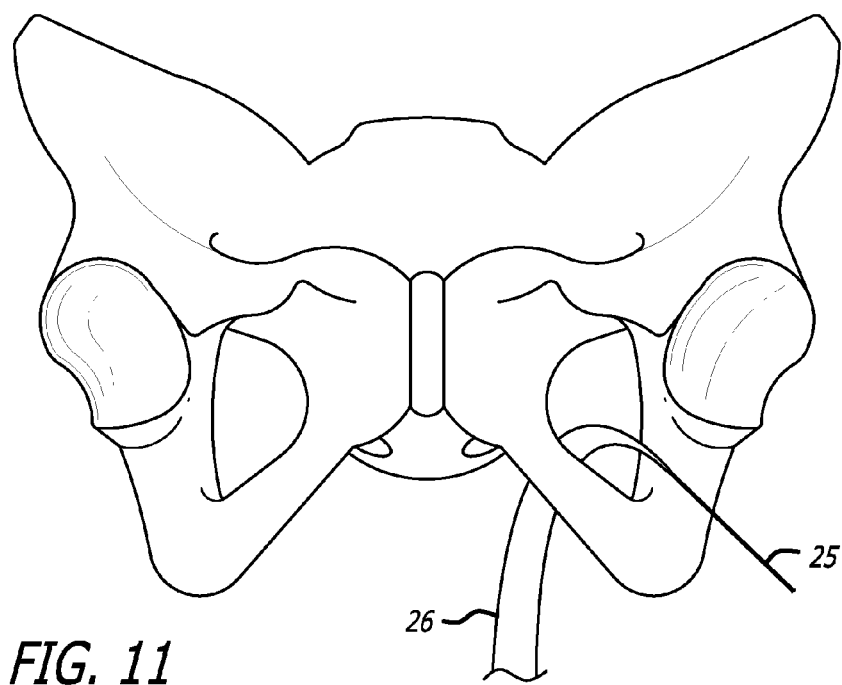
Figure 12:
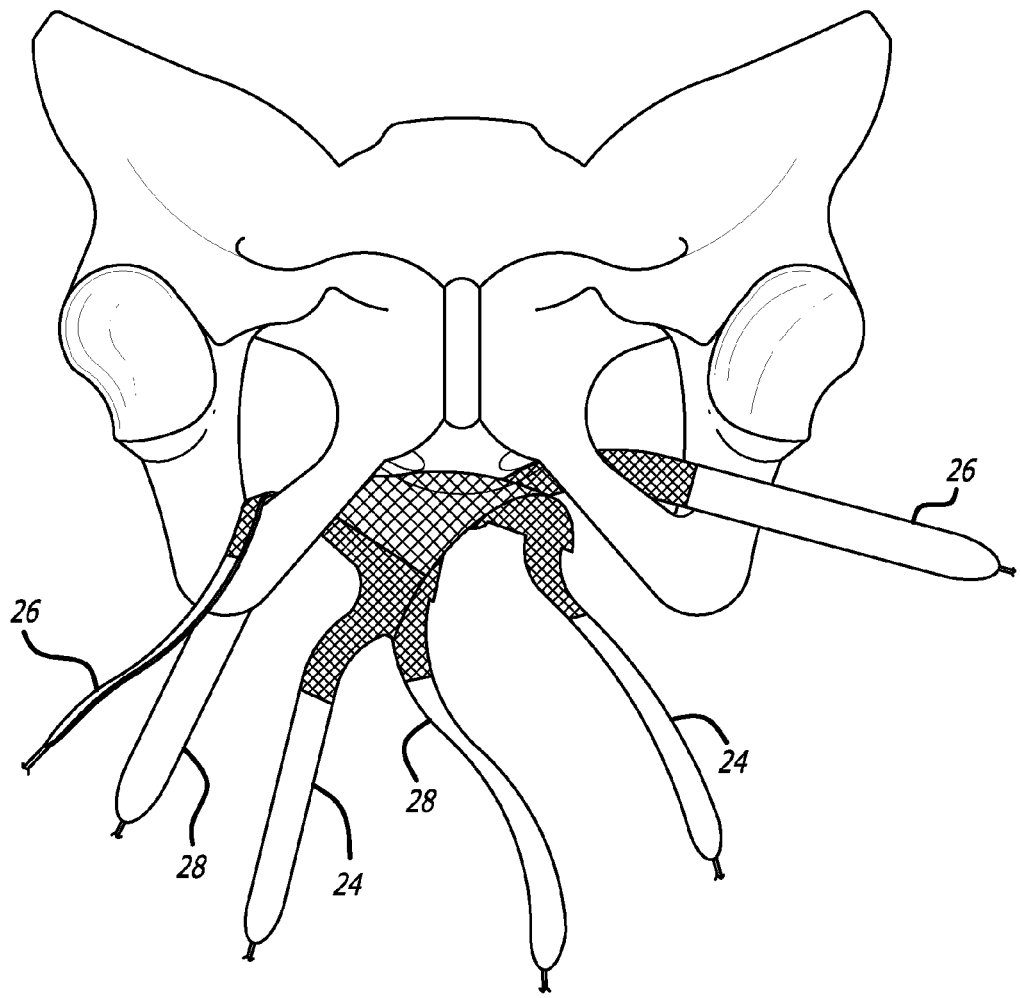

As illustrated in FIG. 11, once the suture loop is loaded onto the inferior introducer 70, the inferior introducer 70 is reverse rotated and retracted while a reverse traction pull is placed on the suture loop. The introducer 70 and second arm 26 are then pulled through the obturator fossa and out the skin incision while care is given to ensure the second arm 26 does not twist during or after placement. These steps are then repeated on the opposite side (FIG. 12). Traction is applied to the second arms 26 to position the implant 10 and body 12 of the implant 10 into the proper location, preferably as close to the vaginal apex as possible. Preferably, the implant 10 is tension free and there are no ridges palpable.

Figure 13:
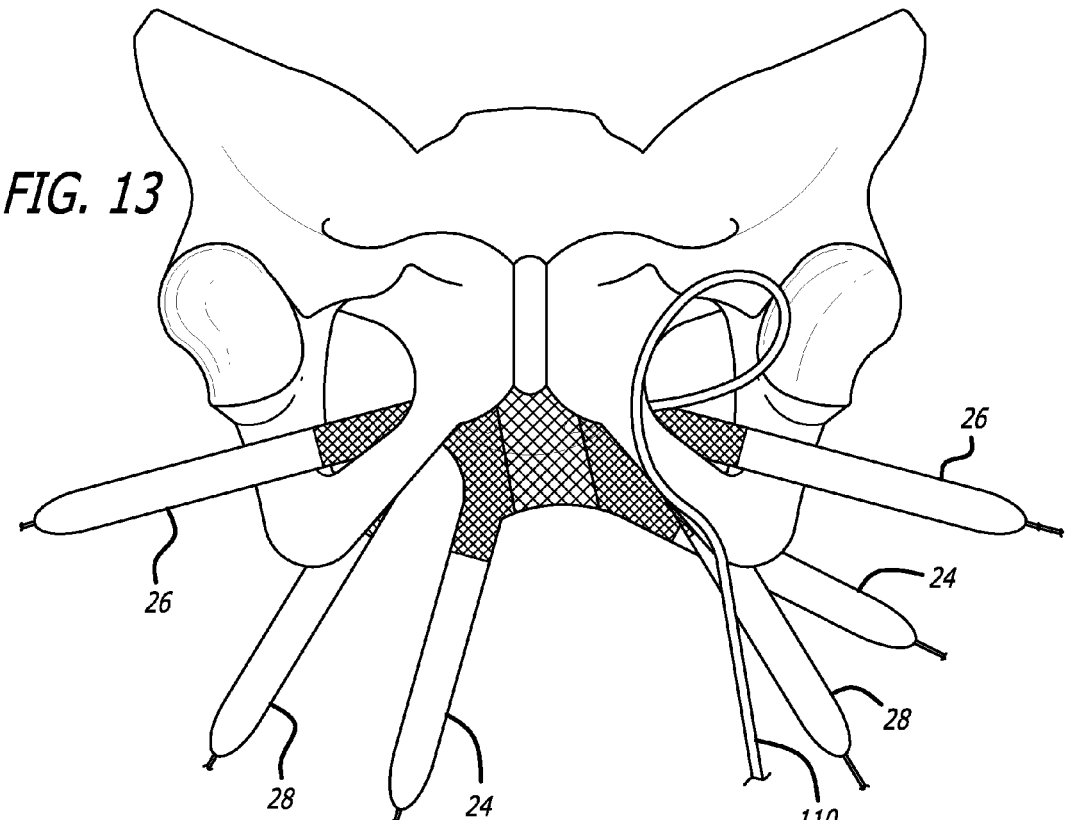
Figure 14:
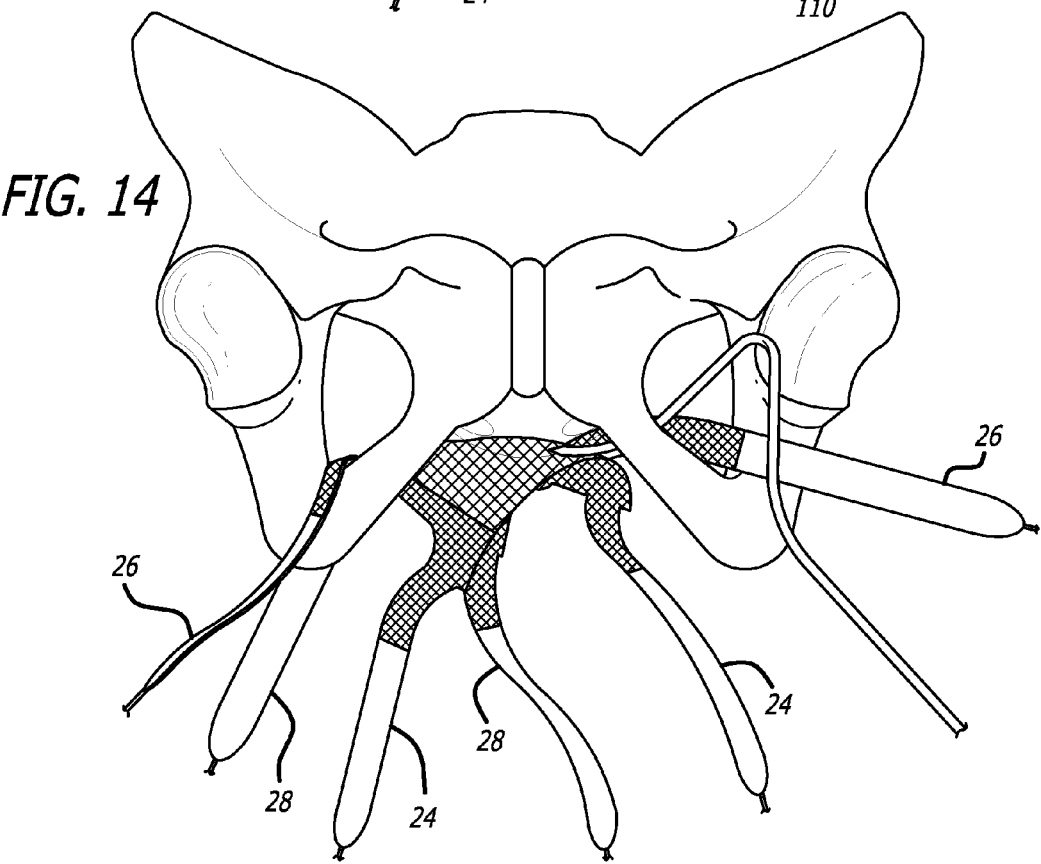

The tip of a right helical introducer 110 is next inserted into the superior groin incision (upper incision) to puncture through the superior medial aspect of the obturator membrane and the introducer tip is directed towards the level of the bladder neck (FIG. 13). The tip of the introducer 110 is identified through palpation and punched through the obturator internus muscle with gentle rotation and pressure. The vaginal index and/or middle fingers may be used to guide the introducer tip through the fascial wall to exit at the level of the bladder neck. The introducer is then rotated to externalize the introducer tip at the introitus (FIG. 14). Care is taken not to hug the pubic ramus. Doing so will make passage of the introducer and the arms more difficult.

Figure 15:
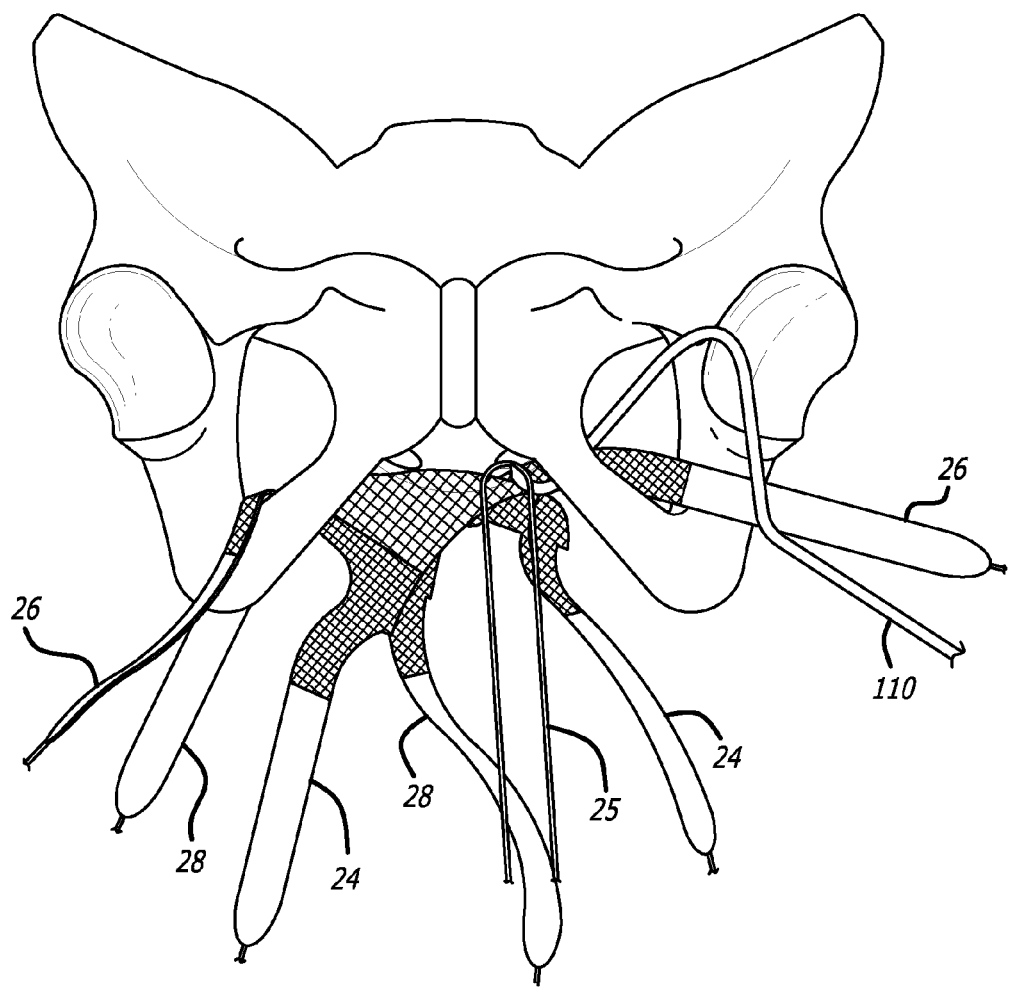
Figure 16:
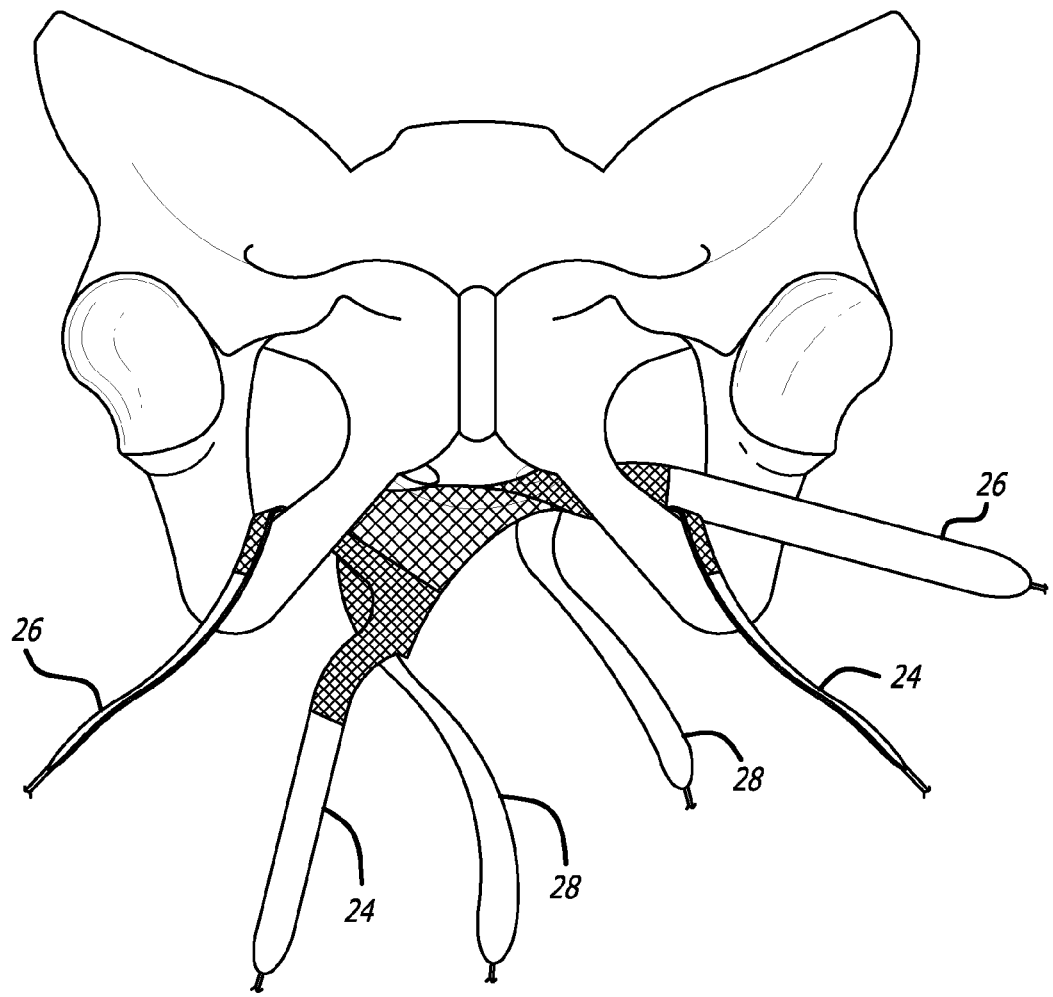

Next, as seen in FIGS. 15-16, a first arm 24 of the implant 10 is identified and a loop 25 of a suture is placed through the notch of the helical introducer 110 or other alternative introducers apparent to one skilled in the art. The right helical introducer 110 is then reverse rotated and retracted as reverse traction pull is placed on the suture loop 25. The introducer 110 and the first arm 24 are pulled through the obturator fossa and out the skin incision taking care that the first arm 24 does not twist during or after placement. These steps are repeated on the opposite side of the patient.

Figure 17:
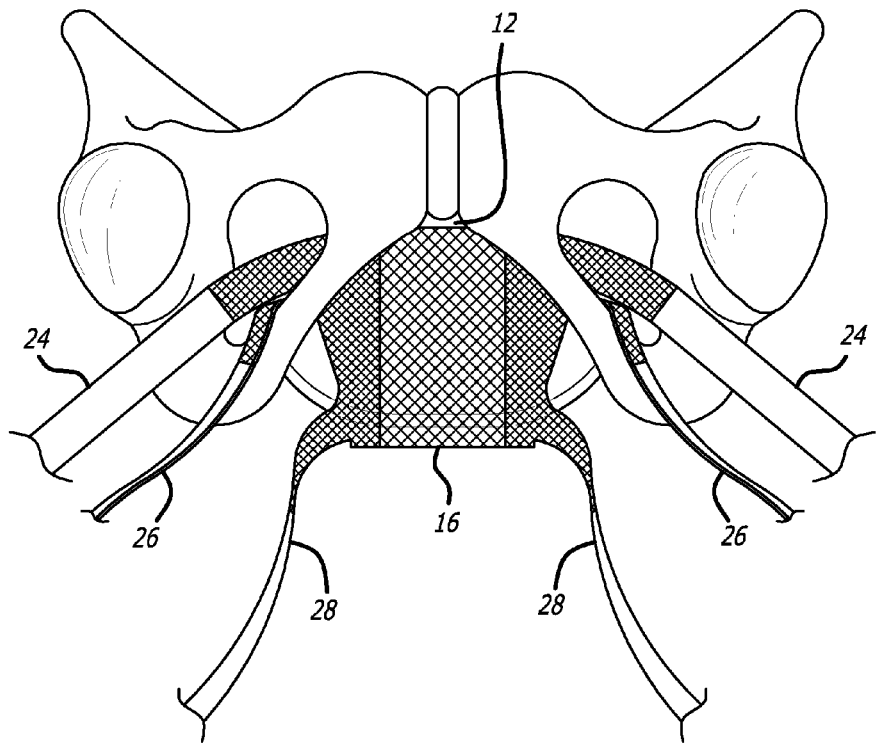

As illustrated in FIG. 17, traction is applied to the first arms 24 to position the implant 10 into the proper location such that the body 12 is substantially near the bladder neck, supporting the bladder without tension. Traction is applied as necessary to the first and second arms 24 or 26 to flatten out any significant folds of the implant 10 material and to ensure complete reduction of the anterior compartment defects. Excess implant 10 material may be trimmed. Cystoscopy should be performed to confirm bladder integrity.

Thereafter, the apex of the vaginal vault can be sutured to the second end 16 of the implant 10. The third arms 28 may be trimmed and attached to the sacrospinous ligament for apical suspension if desired. Instructions on the apical suspension using a intravaginal slingplasty approach via the ischiorectal fossa are described in further detail in the paragraph below.

It is recommended that a rectal probe is used to place the rectum away from the posterior introducer during an intravaginal slingplasty. The vaginal index and middle fingers are important to ensure prevention of damage to the bowel or bladder. In one preferred embodiment of the procedure of the present invention, a intravaginal slingplasty approach, two small 1 cm pararectal incisions are made approximately 2-3 cm lateral and 2-3 cm posterior to the anal opening.

Figure 19:
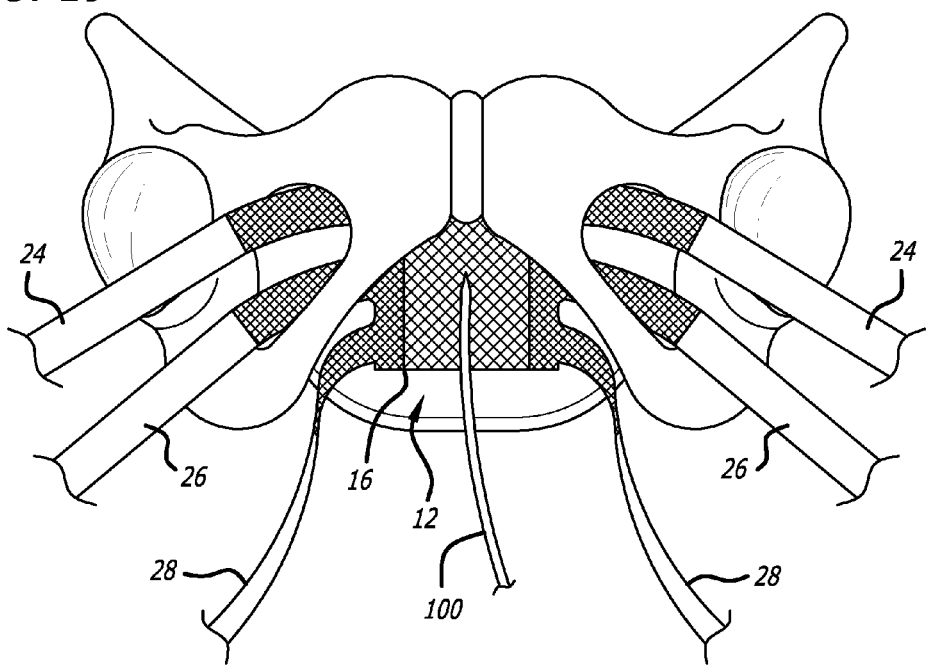
Figure 18:
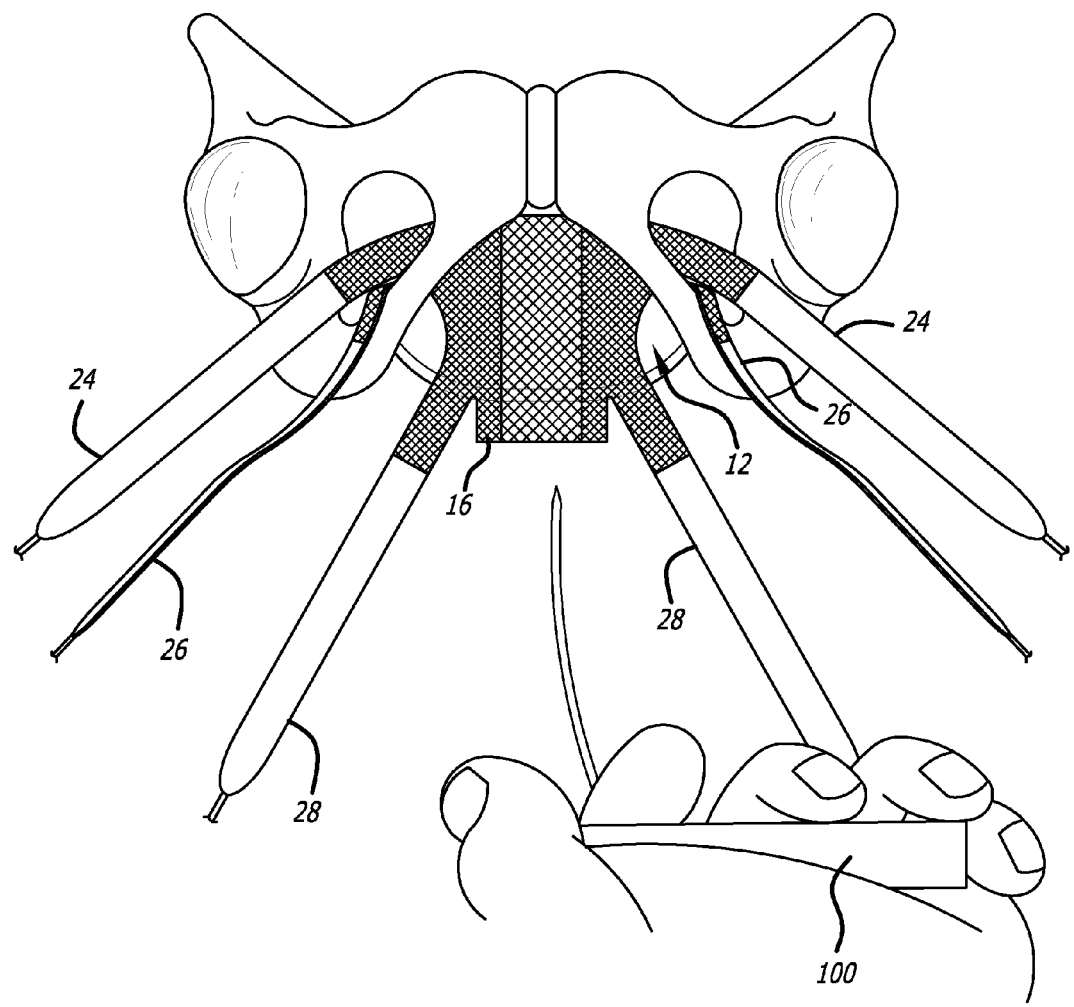

Referring to FIG. 18, a posterior introducer 100 is positioned with the handle vertical and the introducer tip horizontal and parallel to the pelvic floor. The introducer tip is then inserted into one of the pararectal incisions and aimed lateral, away from the rectum, and towards the ischial spine. The tip of the introducer 100 is next passed through the ischiorectal fossa traveling lateral to the posterior wall of the rectum until the introducer tip nears the ischial spine. The handle moves downward to direct the introducer tip upwards approximately 1-2 cm anterior to the ischial spine. As seen in FIG. 19, the tip of the introducer 100 is guided by vaginal finger/s to direct the introducer tip through the levator ani, past the vaginal wall incision, and out towards the introitus to externalize it. Care is taken not to tear the pelvic tissues during this maneuver.

Figure 20:
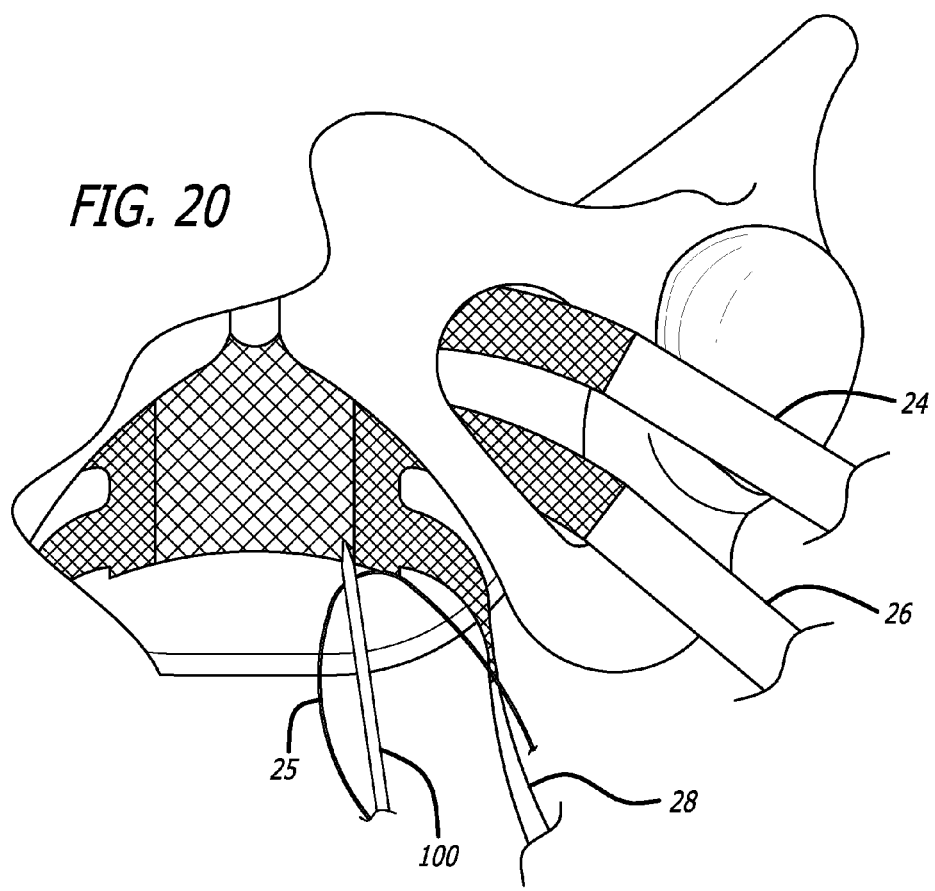
Figure 21:
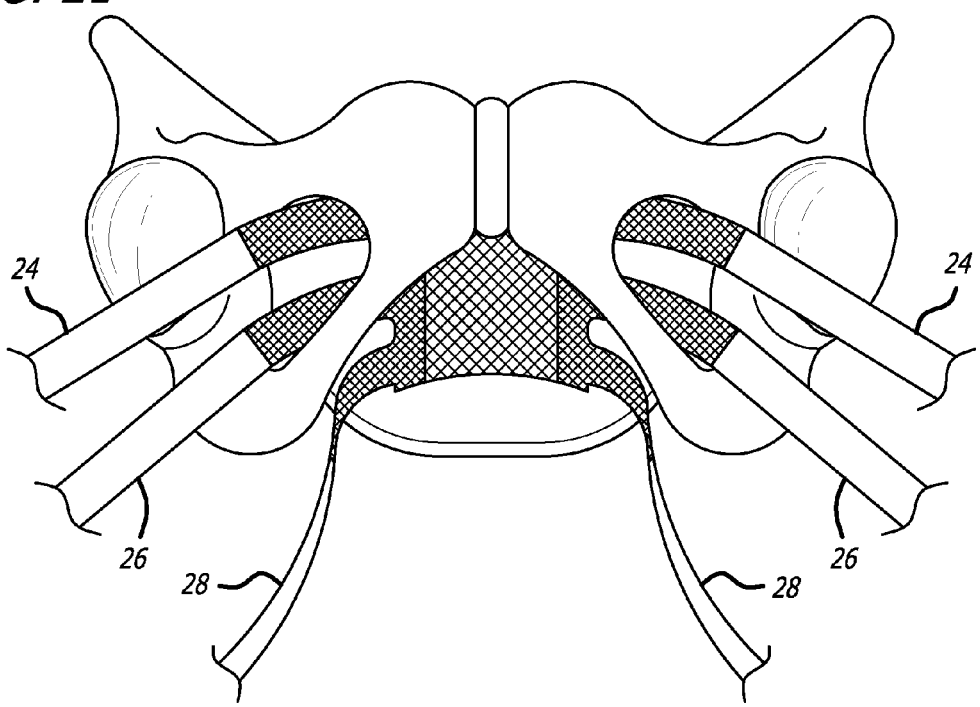

Next, as illustrated in FIG. 20, a third arm 28 of the implant 10 is identified and a loop of a suture is placed through the notch of the posterior introducer 100. The posterior introducer 100 is gently retracted, following its curve, as a reverse traction pull is placed on the suture loop 25. The introducer 100 and the third arm 28 are pulled through the ischiorectal fossa and out the pararectal skin incision, making sure the third arm 28 does not twist during or after placement. These steps are repeated on the opposite side of the body, resulting in the configuration illustrated in FIG. 21.

Next, the apex of the vagina may be sutured to the second end 16 of the implant 10 with the previously placed apical sutures. The cervix may also be sutured to the implant 10 to prevent the prolapse of the cervix, uterus, and vaginal vault. The vagina is pushed to its maximal depth with the examining fingers and given gentle traction on the third arms 28 to remove any slack. If necessary, interrupted sutures may be placed to attach the body 12 of the implant 10 to the levators and to remove excess slack. Sutures should be placed at least 1 cm from the edges of the body 12 of the implant 10. Once satisfied with the implant 10 placement, all arms 24, 26 and 28 of the implant 10 are trimmed below the level of the skin and the incisions are closed. Groin and buttock incisions can be closed with skin glue and vaginal incisions can be closed using a running stitch.

Posterior Compartment Implant

A method of placing a posterior compartment implant 40 as contemplated for use in the present invention is illustrated in FIGS. 22-26 and includes a surgical procedure as follows. Only a posterior introducer 100 (FIG. 7) is needed for this procedure.

A patient is given local, general, spinal or epidural anesthetic. Pre and intra-op and post-op antibiotics are recommended. Pre-op bowel prep is recommended. The patient is placed in dorsal lithotomy stirrups and standard sterile preparation is performed. Vaginal retraction for access and view are recommended, as it will make the procedure easier to perform.

Sterile saline, diluted local anesthetic with epinephrine, diluted vasopressin, or other solution is injected underneath the vaginal mucosa for aqua dissection and help with hemostasis. The injection can be done from the perineum and introitus all the way to the lateral sidewalls and vaginal apex. A midline incision is made in the posterior vaginal wall starting at the introitus and extended to approximately 2-3 cm short of the vaginal cuff or cervix. The vaginal mucosa is dissected away from the rectum laterally to the vaginal sidewalls, and levator ani, and to the ischial spines on both sides and to the sacrospinous ligaments bilaterally.

Three or more interrupted sutures may be placed to the apex of the vagina. These are preferably approximately 1 to 2 cm apart. These will later be attached to the implant 40 for apical support and to prevent an enterocele from forming.

It is recommended that a rectal probe be used to place the rectum away from the posterior introducer 100 during the intravaginal slingplasty. The use of vaginal index and middle fingers are important to ensure prevention of damage to bowel or bladder. Two small 1 cm pararectal incisions are made approximately 2-3 cm lateral and 2-3 cm posterior to the anal opening. The posterior introducer 100 is positioned with the handle vertical and the introducer tip horizontal and parallel to the pelvic floor.

Figure 22:
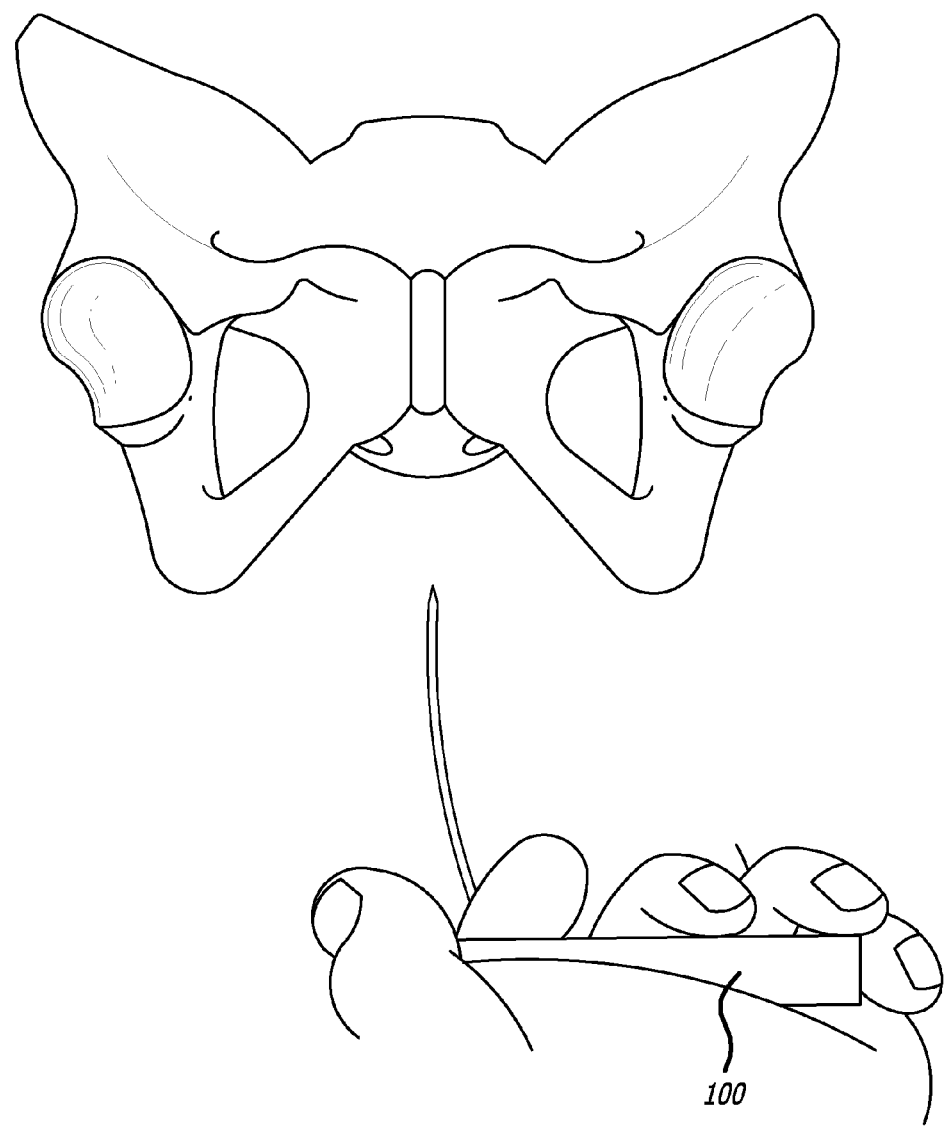
Figure 23:
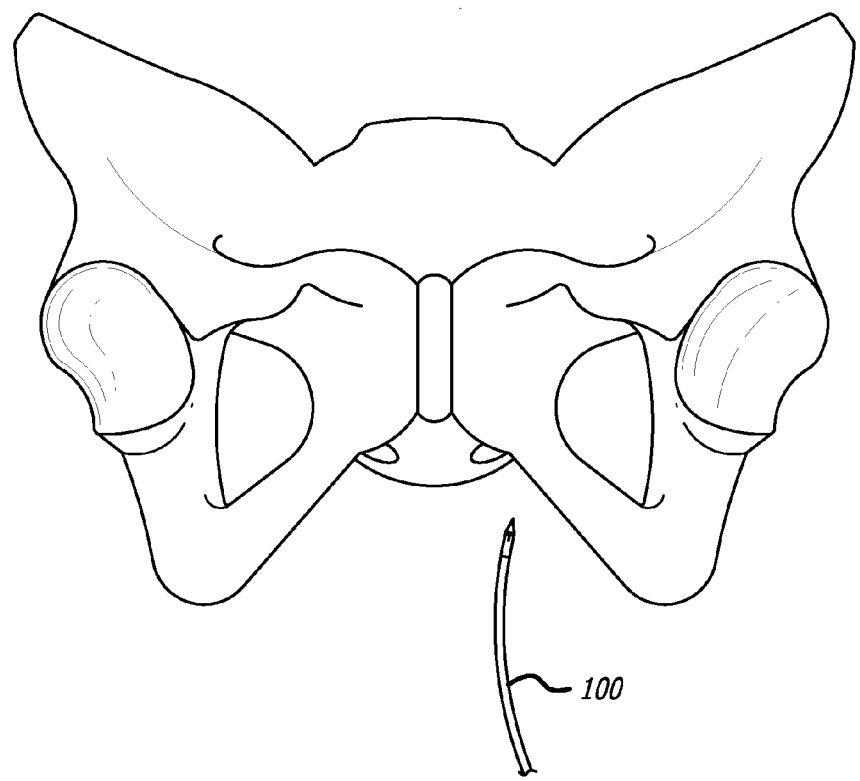

Referring to FIG. 22, the introducer 100 is now inserted into one of the pararectal incisions and aimed lateral, away from the rectum, and towards the ischial spine. The tip of the introducer 100 is passed through the ischiorectal fossa traveling laterally to the posterior wall of the rectum until the tip of the introducer 100 nears the ischial spine. The handle moves downward to direct the introducer tip upwards approximately 1-2 cm anterior to the ischial spine. The introducer tip is guided by vaginal finger/s to direct the introducer tip through the levator ani, past the vaginal wall incision, and out towards the introitus to externalize it (FIG. 23). Care is taken not to tear the pelvic tissues during this maneuver.

Figure 24:
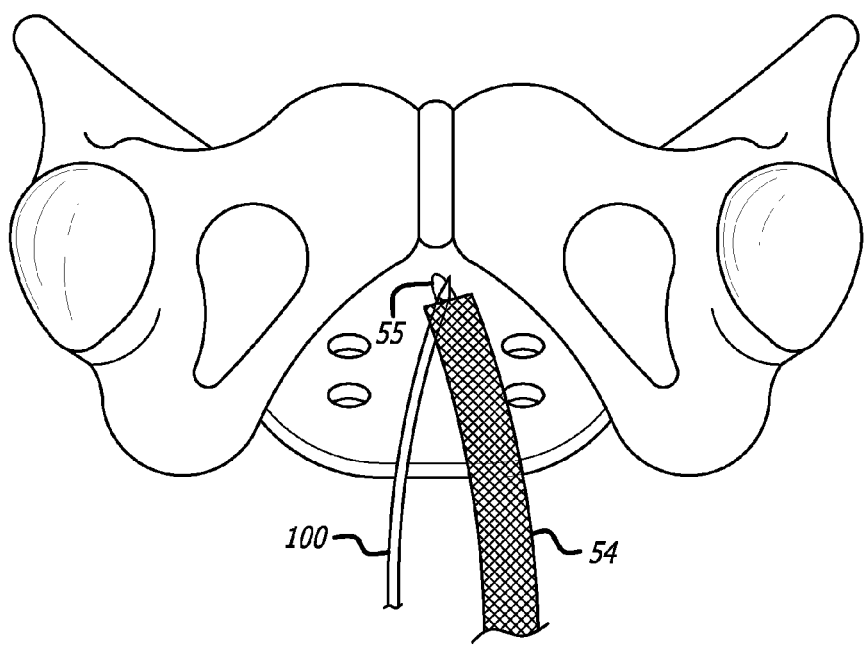
Figure 25:
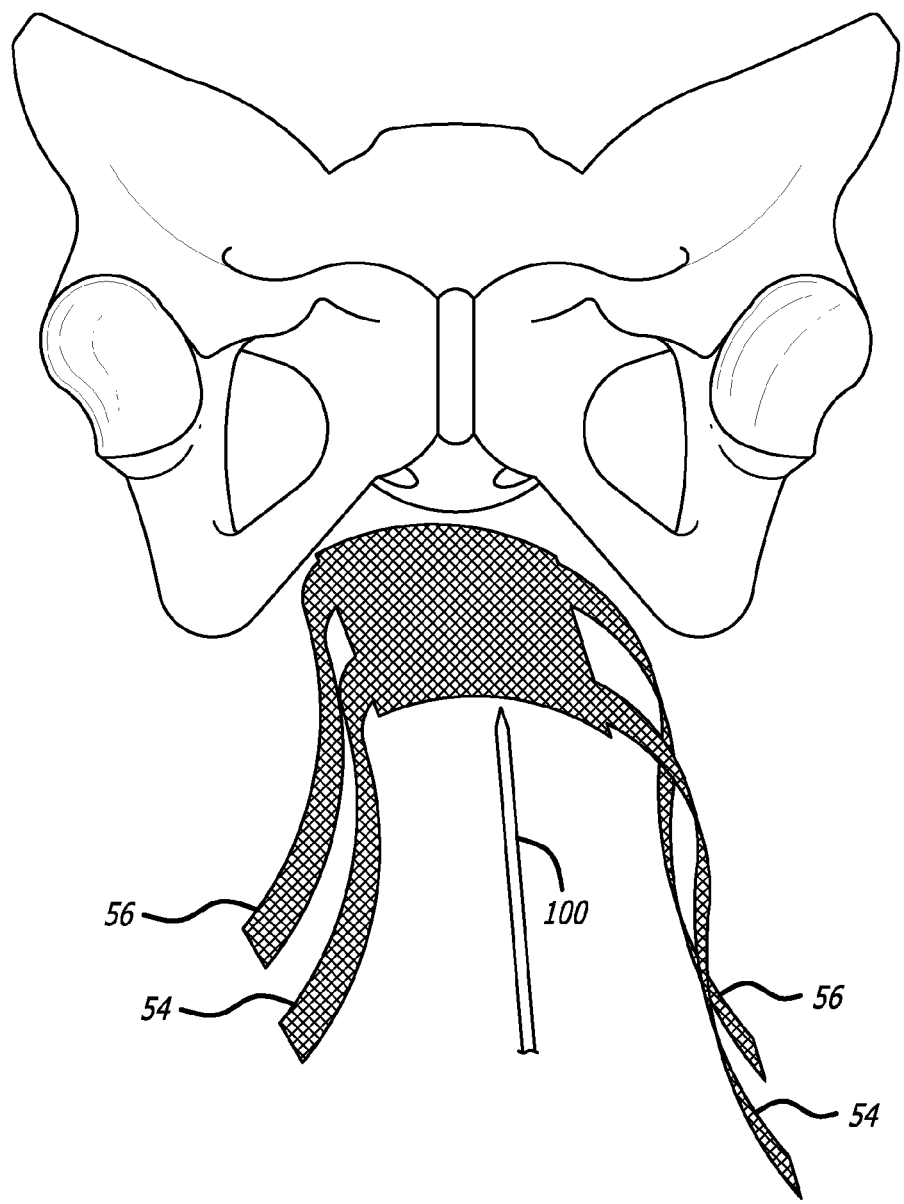

Referring to FIG. 24, a first arm 54 of the implant 10 is identified and a suture loop 55 is placed through the notch of the posterior introducer 100. The posterior introducer 100 is gently retracted, following its curve, as a reverse traction pull on the suture loop is applied. The introducer 100 and the first arm 54 are pulled through the ischiorectal fossa and out the pararectal skin incision, making sure the first arm 54 does not twist during or after placement. These steps are repeated with the other first arm 54 on the opposite side of the patient.

The apex of the vagina may be sutured to the first end 44 of the implant 40 with the previously placed apical sutures. If the patient has a uterus and cervix, the cervix may also be sutured to the implant 40 to prevent the prolapse of the cervix, uterus, and vaginal vault. Gentle traction is applied to the first arms 54 of the implant 40 into the desired position to ensure that the implant 40 and body of the implant 42 are centered, making sure the implant 40 lays flat and tension-free. The second arms 56 may be trimmed off and the second end 46 of the implant 40 can be trimmed and sutured to the perineal body.

If the second arms 56 are not trimmed off and are used as anchors, the following procedure may be employed: The tip of the posterior introducer 100 is inserted into two small 1 cm pararectal incisions approximately 2-3 cm lateral and 2-3 cm posterior to the anal opening and it is pointed towards the vaginal introitus (see FIG. 25). The introducer tip is passed lateral to the anal sphincter and rectum, using fingers in the vagina to guide the introducer tip through the posterior vaginal wall incision at the perineal body and to externalize the tip at the introitus.

Figure 26:
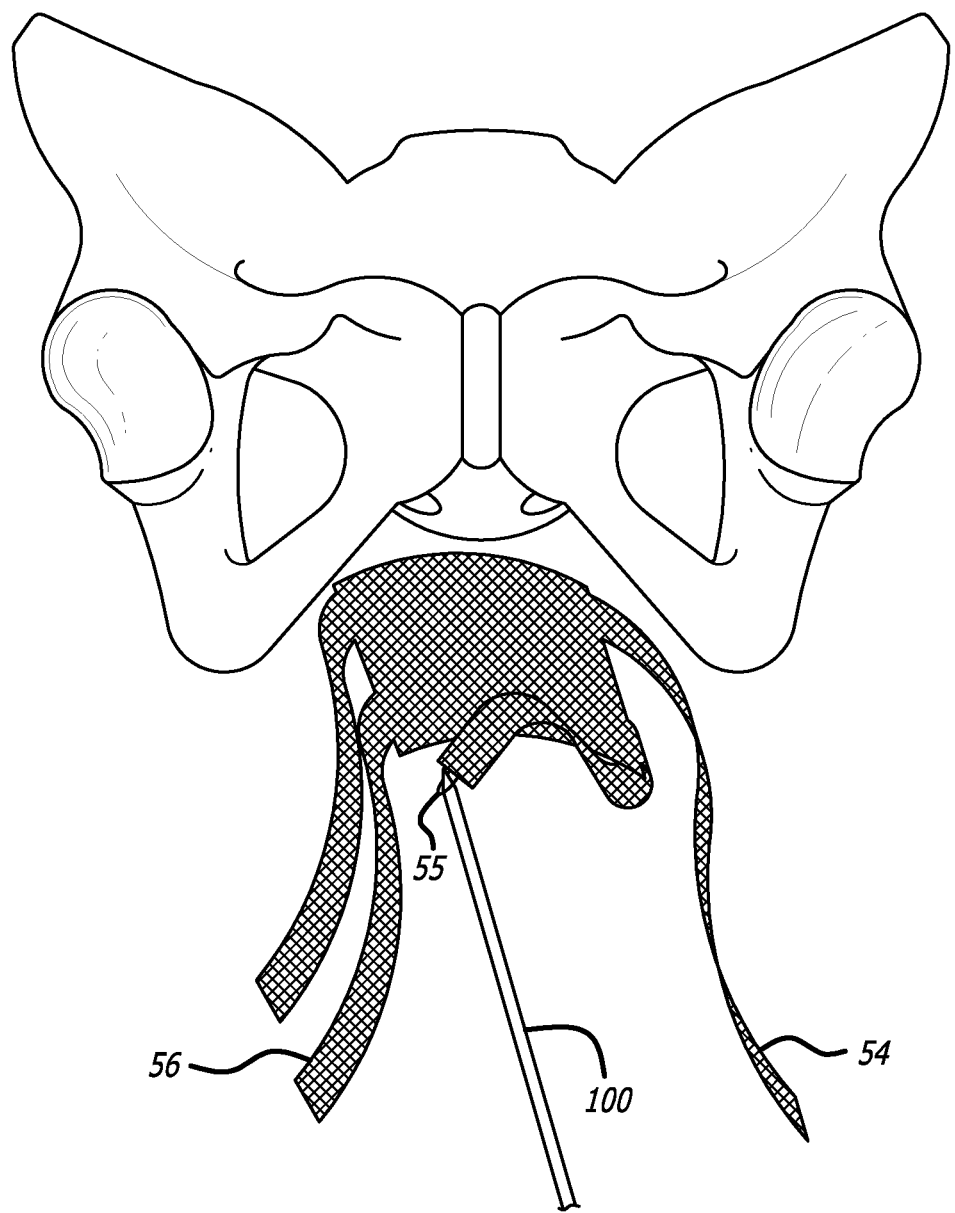

Next, as illustrated in FIG. 26, a second arm 56 of the implant 40 is identified and a loop of a suture 55 is placed through the notch of the posterior introducer 100. The posterior introducer 100 is gently retracted, following its curve, as a reverse traction pull is placed on the suture loop to prevent it from falling out of the notch. The introducer 100 and the second arm 56 are pulled through the pararectal skin incision, making sure the second arm 56 does not twist during or after placement. These steps are repeated on the opposite side of the patient.

The vagina is then pushed to its maximal depth with the examining fingers and gentle traction is placed on the first arms 54 and the second arms 56 to remove any slack and to ensure the implant 40 and body 42 of the implant 40 is centrally located and laying flat. The second end 46 of the body 42 should be positioned right over the perineal body. Trimming of excess lateral and distal implant 40 material can now be performed if needed.

Interrupted sutures may be placed to attach the lateral mesh to the levator ani and to remove excess slack but still maintaining a tension-free repair. Keeping the vagina to its full depth while suturing the lateral edges of the body 42 to the levator ani is ideal. The implant 40 should lay flat over the rectum and/or enterocele with minimal tension. In one preferred embodiment of the present invention, an average of three interrupted sutures per side is used. Preferably, sutures should be placed at least 1 cm from the edges of the body 42 of the implant 40. The section of the implant 40 placed over the perineal body should be the last section of the implant 40 sutured securely with three interrupted sutures. This will prevent a rectocele or enterocele from protruding over the perineal body. Once satisfied with the implant 40 placement, all arms 54, 56 of the implant 40 are trimmed below the level of the skin and the incisions are closed. Pararectal incisions can be closed with skin glue and vaginal incisions can be closed using a running stitch.

As stated above, one aspect of the present invention is that a posterior compartment implant and an anterior compartment implant in accordance with the disclosure above can be jointly used to treat multiple pelvic floor disorders simultaneously. In addition, an implant for treatment of urinary incontinence could also be included in such an operation. For example, a urinary incontinence sling commercialized under the name Desara by the assignee of the present application could also be introduced into the patient during the same treatment using the posterior and anterior compartment implants disclosed herein.

Although the invention has been described in terms of particular embodiments and applications, one of ordinary skill in the art, in light of the teaching, can generate embodiments and modifications without departing from the spirit of or exceeding the scope of the claimed invention. For example, it will be clear to one of ordinary skill in the art how to apply the inventive concepts disclosed herein to the treatment of multiple pelvic support conditions for both male and female patients. Accordingly, it is to be understood that the drawings and descriptions herein are proffered by way of example to facilitate comprehension of the invention and should not be construed to limit the scope thereof.

We claim:

1. A method for placing a pelvic floor disorder implant comprising:
   (a) providing an implant comprising a body portion and at least a pair of arms;
   (b) making a first and second skin incision;
   (c) making a midline anterior vaginal incision;
   (d) directing a distal end of an introducer through said first skin incision;
   (e) puncturing the distal end of the introducer through an obturator membrane;
   (f) directing the distal end of the introducer in a posterior direction to substantially reach an ischial spine;
   (g) extending a first arm of said pair of arms through the midline anterior vaginal incision and attaching the first arm to the distal end of the introducer;
   (h) retracting the introducer and the first arm back through the first skin incision;
   (i) directing the distal end of the introducer through said second skin incision; (j) puncturing the distal end of the introducer through an opposing obturator membrane; (k) directing the distal end of the introducer in a posterior direction to substantially reach an opposing ischial spine; (l) extending a second arm of said pair of arms through the midline anterior vaginal incision and attaching the second arm to the distal end of the introducer; (m) retracting the introducer and the second arm back through the second skin incision;
   (n) securing said body portion of said implant into position so as to treat a pelvic floor disorder.

* * * * *